(12) United States Patent
Liu et al.

(10) Patent No.: US 12,611,665 B2
(45) Date of Patent: Apr. 28, 2026

(54) IN SITU CHROMATIC BIOSENSOR

(71) Applicant: University of Manitoba, Winnipeg (CA)

(72) Inventors: Song Liu, Winnipeg (CA); Sarvesh Logsetty, Winnipeg (CA); Farinaz J. Shariatzadeh, Winnipeg (CA)

(73) Assignee: UNIVERSITY OF MANITOBA, Winnipeg (CA)

( * ) Notice: Subject to any disclaimer, the term of this patent is extended or adjusted under 35 U.S.C. 154(b) by 572 days.

(21) Appl. No.: 18/129,212

(22) Filed: Mar. 31, 2023

(65) Prior Publication Data

US 2024/0326039 A1    Oct. 3, 2024

(51) Int. Cl.
B01L 3/00        (2006.01)
A61B 5/00        (2006.01)
C12Q 1/04        (2006.01)
C12Q 1/44        (2006.01)

(52) U.S. Cl.
CPC ........... B01L 3/5023 (2013.01); A61B 5/445 (2013.01); C12Q 1/04 (2013.01); C12Q 1/44 (2013.01); B01L 2200/16 (2013.01); B01L 2300/069 (2013.01)

(58) Field of Classification Search
CPC .............. B01L 3/5023; B01L 2200/16; B01L 2300/069; A61B 5/445; G01N 21/78; C12Q 1/04; C12Q 1/44
See application file for complete search history.

(56) References Cited

U.S. PATENT DOCUMENTS

2021/0338596 A1*  11/2021  Liu ................... A61F 13/01017
2022/0047523 A1*   2/2022  Liu ......................... A61L 15/46

OTHER PUBLICATIONS

A. Piriya V.S. et al., "Colorimetric sensors for rapid detection of various analytes", Mater. Sci. Eng. C, vol. 78, pp. 1231-1245, 2017, 15 pages.

(Continued)

*Primary Examiner* — Michael L Hobbs
(74) *Attorney, Agent, or Firm* — CALDERON SAFRAN & WRIGHT P.C.

(57)            ABSTRACT

A biosensor for real-time monitoring of a wound can provide valuable data regarding the presence of bacteria. A nanofibrous biosensor is provided for monitoring wound status at the point of care. The colorimetric biosensor changes color in response to low levels of bacteria and fungi, making it visible to unaided and untrained eyes. A colorimetric probe is a hemicyanine dye that changes color from yellow to green in the presence of lipase. Dye is incorporated into a shell composition of core-shell nanofibers made of polyurethane and polyvinylpyrrolidone. As a means of increasing the biosensor's sensitivity, the alignment of nanofibers is controlled and a surfactant added to the shell (e.g., Tween 80). Alignment of nanofiber enables better localization, and Tween 80 increases lipase activity, which facilitates near immediate color changes above critical levels of *Staphylococcus aureus, Pseudomonas aeruginosa, Candida albicans*, and *Candida aureus*. All ESKAPEE bacteria are detected within 2 hours.

6 Claims, 13 Drawing Sheets
(12 of 13 Drawing Sheet(s) Filed in Color)

(56)                    References Cited

OTHER PUBLICATIONS

A. Pusta et al., "Wearable sensors for the detection of biomarkers for wound infection", Biosensors, vol. 12, No. 1, pp. 1-20, 2022; 20 pages.

C. Carrasco-López et al., "Activation of bacterial thermo alkalophilic lipases is spurred by dramatic structural rearrangements", J. Biol. Chem., vol. 284, No. 7, pp. 4365-4372, 2009, 8 pages.

C. Leclech et al., "Is there a universal mechanism of cell alignment in response to substrate topography?", Cytoskeleton, vol. 78, No. 6, pp. 284-292, Jun. 2021; 9 pages.

D. G. Metcalf et al., "Elevated wound fluid pH correlates with increased risk of wound infection", Wound Med., vol. 26, No. 1, p. 100166, 2019, 11 pages.

D. Kim et al., "Colorimetric Systems for the Detection of Bacterial Contamination?: Strategy and Applications", Biosensors, vol. 12, No. 532, 2022; 29 pages.

E. Abaházi et al., "Additives enhancing the catalytic properties of lipase from burkholderia cepacia immobilized on mixed-function-grafted mesoporous silica gel", Molecules, vol. 19, No. 7, pp. 9818-9837, 2014, 20 pages.

F. I. Khan et al., "The lid domain in lipases: Structural and functional determinant of enzymatic properties", Front. Bioeng. Biotechnol., vol. 5, No. MAR, pp. 1-13, 2017, 13 pages.

G. Landa et al., "Selective point-of-care detection of pathogenic bacteria using sialic acid functionalized gold nanoparticles", Talanta, vol. 234, p. 122644, 2021; 10 pages.

H. Singh et al., "Lipase-Responsive Electrospun Theranostic Wound Dressing for Simultaneous Recognition and Treatment of Wound Infection", ACS Appl. Bio Mater., vol. 2, No. 5, pp. 2028-2036, 2019; 9 pages.

H. Tang et al., "Understanding the cellular responses based on low-density electrospun fiber networks", Mater. Sci. Eng. C, vol. 119, p. 111470, Feb. 2021, 11 pages.

J. Bender et al. "Lipases as Pathogenicity Factors of Bacterial Pathogens of Humans", in Handbook of Hydrocarbon and Lipid Microbiology, Berlin, Heidelberg: Springer Berlin Heidelberg, 2010, pp. 3241-3258, Abstract; 1 page.

J. Feng et al., "The surfactant tween 80 enhances biodesulfuriza-tion", Appl. Environ. Microbiol., vol. 72, No. 11, pp. 7390-7393, 2006, 4 pages.

J. G. S. Mala et al., "Understanding structural features of microbial lipases—An overview", Anal. Chem. Insights, vol. 2008, No. 3, pp. 9-19, 2008; 11 pages.

J. Santhanalakshmi et al., "Solvent effects on reverse micellisation of Tween 80 and Span 80 in pure and mixed organic solvents", Proc. Indian Acad. Sci. Chem. Sci., vol. 109, No. 1, pp. 27-38, 1997, 12 pages.

J. Xie et al., "The effects of alignment and diameter of electrospun fibers on the cellular behaviors and osteogenesis of BMSCs", Mater. Sci. Eng. C, vol. 120, p. 111787, Jan. 2021, 11 pages.

K. Kiti et al., "The potential use of colorimetric pH sensor from Clitoria ternatea flower for indicating bacterial infection in wound dressing application", Microchem. J., vol. 177, p. 107277, Feb. 2022, 9 pages.

L. Gwynne et al., "TCF-ALP: A fluorescent probe for the selective detection of: Staphylococcus bacteria and application in •"smart" wound dressings", Biomater. Sci., vol. 9, No. 12, pp. 4433-4439, 2021; 7 pages.

L. Gwynne et al., "The Evaluation of Ester Functionalised TCF-Based Fluorescent Probes for the Detection of Bacterial Species", Isr. J. Chem., vol. 61, No. 3-4, pp. 234-238, 2021, 5 pages.

L. J. Bessa et al., "Bacterial isolates from infected wounds and their antibiotic susceptibility pattern: some remarks about wound infec-tion", Int. Wound J., vol. 12, No. 1, pp. 47-52, 2015, 6 pages.

M. Dong et al., "A bacteria-triggered wearable colorimetric band-aid for real-time monitoring and treating of wound healing", J. Colloid Interface Sci., vol. 610, pp. 913-922, 2022; 10 pages.

M. Naseri et al., "Rapid Detection of Gram-Positive and-Negative Bacteria in Water Samples Using Mannan-Binding Lectin-Based Visual Biosensor", ACS Sensors, vol. 7, No. 4, pp. 951-959, 2022; 9 pages.

M.-H. Xiong et al., "Delivery of antibiotics with polymeric par-ticles", Adv. Drug Deliv. Rev., vol. 78, pp. 63-76, Nov. 2014, 14 pages.

N. A. binte Mohamed Salleh et al., "Detecting bacterial infections in wounds: a review of biosensors and wearable sensors in com-parison with conventional laboratory methods", Analyst, pp. 1756-1776, 2022; 21 pages.

N. Asatiani et al., "Evaluation of Fiber Orientation of Ac and Dc Electrospun Plcl Nanofibrous Layers", Nanocon Conf. Proc.—Int. Conf. Nanomater., pp. 240-245, 2021, 6 pages.

N. H. Astuti et al., "The Porosity Calculation of Various Types of Paper Using Image Analysis", J. Pendidik. Fis. Indones., vol. 14, No. 1, pp. 46-51, 2018, 6 pages.

N. Pan et al., "Color-changing smart fibrous materials for naked eye real-time monitoring of wound pH", J. Mater. Chem. B, vol. 7, No. 16, pp. 2626-2633, 2019, Abstract; 2 pages.

N. T. Thet et al., "SPACE Swab: Point-of-Care Sensor for Simple and Rapid Detection of Acute Wound Infection", ACS Sensors, vol. 5, No. 8, pp. 2652-2657, Aug. 2020; 6 pages.

P. G. Bowler et al., "Wound microbiology and associated approaches to wound management", Clin. Microbiol. Rev., vol. 14, No. 2, pp. 244-269, 2001, 26 pages.

R. Kurpanik et al., "Effect of Ionic and Non-Ionic Surfactant on Bovine Serum Albumin Encapsulation and Biological Properties of Emulsion-Electrospun Fibers", Molecules, vol. 27, No. 10, p. 3232, 2022, 24 pages.

S. Currie et al., "Highly Sensitive Bacteria-Responsive Membranes Consisting of Core-Shell Polyurethane Polyvinylpyrrolidone Electrospun Nanofibers for In Situ Detection of Bacterial Infections", ACS Appl. Mater. Interfaces, vol. 12, No. 41, pp. 45859-45872, Oct. 2020, 14 pages.

S. P. Miguel et al., "Electrospun polymeric nanofibres as wound dressings: A review", Colloids Surfaces B Biointerfaces, vol. 169, pp. 60-71, 2018, 12 pages.

T. Fu et al., "Next-Generation Diagnostic Wound Dressings for Diabetic Wounds", ACS Meas. Sci. Au, Jul. 2022, 8 pages.

T. Xu et al., "Properties of Electrospun Aligned Poly(lactic acid)/ Collagen Fibers With Nanoporous Surface for Peripheral Nerve Tissue Engineering", Macromol. Mater. Eng., p. 2200256, Jul. 2022, 11 pages.

W. G. P. Eardley et al., "Infection in conflict wounded", Philos. Trans. R. Soc. B Biol. Sci., vol. 366, No. 1562, pp. 204-218, 2011, 16 pages.

W. Yao et al., "A Valuable Product of Microbial Cell Factories: Microbial Lipase", Front. Microbiol., vol. 12, No. September, pp. 1-16, 2021, 16 pages.

X. Gao et al., "Metabolism-Triggered Colorimetric Sensor Array for Fingerprinting and Antibiotic Susceptibility Testing of Bacteria", Anal. Chem., 2021; 10 pages.

Y. Gao et al., "Gelatin-based photonic hydrogels for visual detection of pathogenic Pseudomonas aeruginosa", Sensors Actuators, B Chem., vol. 329, No. Oct. 2020, p. 129137, 2021, 8 pages.

Y. Li et al., "Multifunctional Fibroblasts Enhanced via Thermal and Freeze-Drying Post-treatments of Aligned Electrospun Nanofiber Membranes", Adv. Fiber Mater., vol. 3, No. 1, pp. 26-37, Feb. 2021; 33 pages.

Y. Y. Liu et al., "Enhancing effect of Tween-80 on lipase perfor-mance in enantioselective hydrolysis of ketoprofen ester", J. Mol. Catal.—B Enzym., vol. 10, No. 5, pp. 523-529, 2000, 7 pages.

Z. Jia et al., "Multiplexed detection and differentiation of bacterial enzymes and bacteria by color-encoded sensor hydrogels", Bioact. Mater., vol. 6, No. 12, pp. 4286-4300, 2021; 15 pages.

Z. Petkovsek et al., "Virulence Potential of Escherichia coli Isolates from Skin and Soft Tissue Infections", J. Clin. Microbiol., vol. 47, No. 6, pp. 1811-1817, Jun. 2009, 2 pages.

* cited by examiner

| Bacteria | Threshold Concentration CFU/cm² | Exposure time |
|---|---|---|
| *E. coli* | 4.20 E+05 | 1 hr |
| MRSA | 2.77 E+04 | Immediate |
| *P. a* | 3.17 E+04 | Immediate |

| Bacteria | concentration CFU/cm² | W | | T0.1 | | T0.5 | | T2 | | T4 | |
|---|---|---|---|---|---|---|---|---|---|---|---|
| | | Initial | Final | Initial | Final | Initial | Final | Initial | Final | Initial | Final |
| E. coli | 4.2E+05 | | | | | | | | | | |
| P. a | 3.2E+04 | | | | | | | | | | |
| MRSA | 2.8E+04 | | | | | | | | | | |
| Mixed | ≥1.0E+08 | | | | | | | | | | |
| Control | TSA | | | | | | | | | | |

FIG. 5

| | R | W | T0.5 |
|---|---|---|---|
| Before Bacterial exposure | | | |
| Alignment | Random | Cross-Aligned | Cross-Aligned |
| After bacterial exposure | | | |
| Bacteria concentration CFU/cm² | 5.31E+08 | 5.23E+08 | 5.21E+08 |
| Attached bacteria Bacteria number/cm² | 1.53E+07 | 6.17E+07 | 7.04E+07 |

FIG. 10

| | Initials | | | After 30 min | | | ΔE | | |
|---|---|---|---|---|---|---|---|---|---|
| Samples | R | W | T0.5 | R | W | T0.5 | R | W | T0.5 |
| MRSA 6.4E+06 | | | | | | | 13.849 | 14.004 | 14.341 |
| P. *a* 1.7E+06 | | | | | | | 13.135 | 13.135 | 13.727 |
| P.*a* + MRSA | | | | | | | 13.073 | 13.219 | 14.312 |

IN SITU CHROMATIC BIOSENSOR

FIELD OF INVENTION

The present disclosure relates generally to chromatic biosensors for use in diagnostics and wound healing.

Wound infection is a global healthcare issue that affects the healing process. Appropriate wound dressing material can reduce the risk of infection by reducing or eliminating the invasion of pathogens. The use of antibacterial materials or agents in wound dressings can reduce risk of infection. Early detection of bacterial presence at low thresholds enables early intervention to prevent worsening of infection.

All of the references, patents, and patent applications that are referred to herein are incorporated by reference in their entirety as if they had each been set forth herein in full. Note that this application is one in a series of applications by the Applicant covering methods and apparatus for enabling biomedical applications of nanofibers. The term "fiber" and the term "nanofiber" may be used interchangeably, and neither term is limiting. The terms "Tween" and "Triton" are trade names for non-ionic surfactants and neither term is limiting. Tween® is also known generically as polysorbate. The term "Tween" is a registered trademark of CRODA AMERICAS LLC. The term "Triton" is also known generically as octoxynol-9. The term "Triton" is a registered trademark of Dow Chemical Company. Both Tween® and Triton® branded surfactants are available from distributors such as Sigma-Aldrich and each is described as a non-ionic detergent and surfactant. The disclosure herein goes beyond that needed to support the claims of the particular invention set forth herein. This is not to be construed that the inventor is thereby releasing the unclaimed disclosure and subject matter into the public domain. Rather, it is intended that patent applications will be filed to cover all of the subject matter disclosed below. Also, please note that the terms frequently used below "the invention" or "this invention" is not meant to be construed that there is only one invention being discussed. Instead, when the terms "the invention" or "this invention" are used, it is referring to the particular invention being discussed in the paragraph where the term is used.

BACKGROUND

Wound infection is one of the major causes of non-healing wounds. The common infection detection techniques require highly trained personnel besides being time-consuming or expensive, such as swabbing/plating and polymerase chain reaction (PCR), respectively. Overall, the lack of a sensitive bedside infection detection technique necessitates drastic antibiotic usage, increasing bacterial resistance and compromising patients' health. In the past few years, there has been a growing interest in using Biosensors for in situ detection of bacterial infection as a means to identify infection at its inception. Although a commercially available low cost, rapid and sensitive biosensor for infection detection has not been developed yet. Considerable attention has been paid to colorimetric-based biosensors for in situ rapid diagnosis quite recently. The in situ colorimetric-based biosensors' advantages are low-cost, easy handling, easy to store, and easy readout, which can be observed with the naked and untrained eyes in real-time without requiring dressing changes or wound sampling. The most commonly used colorimetric biosensors depend on small molecules that undergo structural changes due to the presence of bacteria or infection to change their color. Bacteria and infection are associated with internal stimuli such as alkali pH, low oxygen level and extracellular bacterial enzymes. These stimuli have been used to trigger a response of biosensors. Organic dyestuffs with functional groups responsive to those internal stimuli have been used in those biosensors to deliver a visual signal.

The biosensors can be fabricated with a wide range of materials, such as natural and synthetic polymers, metallic and polymeric nanoparticles with different architectures and shapes. Most nanoparticle-based biosensors are used to detect bacteria in an aqueous suspension. For instance, metallic nanoparticles such as modified gold and silver nanoparticles can detect infection and change their color due to interaction with bacteria, followed by agglomeration and changes in their size. However, the toxicity and fate of nanoparticles in our bodies are still debatable. Moreover, solution-based biosensors cannot be used as in situ biosensors. Most in situ biosensors are membrane-based and can be hydrogels, films or nanofibrous membranes. As mentioned, different internal stimuli can be used to detect bacteria presence. One group of well-developed in situ colorimetric biosensors are pH-based sensors. The pH of natural skin ranges from 4.0 to 6.0, and when skin is injured, the wound exudate increases the pH to 7.0-7.4, and if infection occurs, the pH increases to 8.0 and higher due to byproducts of bacteria. Therefore, incorporating materials that change their color at different pH are used for bacteria detection during wound healing Although pH undergoes changes during the wound healing steps and the presence of infection, it also be altered due to environmental conditions such as cleaning wounds procedure, or due to the presence of topical antimicrobials and metabolic factors. Therefore, the pH cannot be a reliable indicator solely. Bacterial toxin and extracellular enzymes are the most reliable indicators for infection detection. Bacteria secrete different virulence factors, such as proteins and enzymes. And among these secretions, lipase is one of the common factors responsible for diseases and infections.

The role of fibers alignment on different cellular behavior, such as neural cells, fibroblasts, and even stem cells, has been investigated vastly. Fiber alignment in a fibrous membrane can affect cell migration, adhesion or even differentiation. However, the role of substrate (fibers) alignment on bacteria cells has not been reported.

U.S. patent application Ser. No. 17/487,285 filed Sep. 28, 2021 by the University of Manitoba (Applicant), entitled "COLOR-CHANGING ANTIBACTERIAL NANOFIBER" by the same Applicant hereof discloses a color-changing membrane for bacteria detection based on bacteria secretion. The nanofibrous membrane (based on polyurethane) containing a hemicyanine (HCy) dye can change its color from yellow to green due to the presence of secreted lipase from bacteria in infected wounds. Lipase cleaves the ester bond in HCy, facilitating more efficient intramolecular charge transfer that causes color changes. In a recent study (S. Currie, F. J. Shariatzadeh, H. Singh, S. Logsetty, and S. Liu, "Highly Sensitive Bacteria-Responsive Membranes Consisting of Core-Shell Polyurethane Polyvinylpyrrolidone Electrospun Nanofibers for In Situ Detection of Bacterial Infections," *ACS Appl. Mater. Interfaces*, vol. 12, no. 41, pp. 45859-45872, October 2020) published by the Applicant, it was reported that incorporating a dopant polymer (polyvinyl pyrrolidone) into the shell structure of nanofibers could enhance the sensitivity of detection (2 hr. exposure: 2.5E+05 CFU/cm$^2$ *P. aeruginosa* and 1.0E+06 CFU/cm$^2$ MRSA.)

Real-time monitoring and assessment of a wound can provide valuable data regarding the presence of bacteria. There is significant interest in the use of biosensors for this purpose. Detecting bacteria early can decrease the risk of infection and prevent the unnecessary use of antibiotics, which contribute to the development of bacterial resistance. However, due to the need for advanced technology and special training, as well as the high cost associated with high-tech biosensors, their application for wound monitoring and assessment is hindered. A biosensor is needed that can monitor wound status to assess the level of bacterial presence in situ and overcome the mentioned shortcomings.

SUMMARY

It is an object of the present invention to obviate or mitigate at least one disadvantage of previous biosensors intended for wound monitoring or assessment.

It is an object of the present invention to accelerate colorimetric response in a biosensor to the presence of pathogens in a wound.

It is an object of the present invention to provide a colorimetric biosensor usable for in situ monitoring and assessment of the presence of pathogens in a wound by changing its color in response to low levels of bacteria, presenting a vivid visible indication of infection to naked and untrained eyes.

There is provided a polymeric, core-shell nanofiber comprising: a colorimetric probe incorporated in the shell that changes color in the presence of pathogens a tunable threshold.

In one aspect, there is provided a polymeric, core-shell nanofiber comprising a hemicyanine dye as a colorimetric probe that changes its color from yellow to green in the presence of secreted lipase from bacteria and fungi.

In one aspect, there is provided a polymeric, core-shell nanofiber comprising a hemicyanine dye incorporated into a shell composition of core-shell nanofibers made of polyurethane and polyvinylpyrrolidone; core: PU, shell: PU/PVP/ HCy nanofibers.

In another aspect, there is provided a polymeric, core-shell nanofiber comprising a hemicyanine dye and a surfactant incorporated into a shell composition of core-shell nanofibers.

In one aspect, a biosensor is provided comprising a core-shell nanofiber having a colorimetric probe incorporated in the shell, wherein the colorimetric probe changes color in the presence of pathogens at a tunable specific threshold.

In another aspect, a biosensor is provided comprising a core-shell nanofiber comprising polyurethane, polyvinylpyrrolidone, and a surfactant.

In one aspect, a biosensor is provided comprising core-shell nanofibers with a hemicyanine dye and a surfactant (e.g., Tween 80) incorporated into a shell composition of the core-shell nanofibers.

In one aspect, a biosensor is provided comprising a colorimetric probe that changes color when exposed to pathogens in the range of 1.0E+06 CFU/cm$^2$ and 2.5E+05 CFU/cm$^2$ for Methicillin resistant *Staphylococcus aureus* (MRSA) and in the range of 2.0E+04 CFU/cm$^2$ and 3.5E+04 CFU/cm$^2$. *Pseudomonas aeruginosa.*

In another aspect, a biosensor is provided comprising a colorimetric probe that changes color when exposed to pathogens exceeding 2.0E+04 CFU/cm$^2$ for Methicillin resistant *Staphylococcus aureus* (MRSA), 3.0E+04 CFU/ cm$^2$ for *Pseudomonas aeruginosa,* 1.0E+05 CFU/cm$^2$ for *Candida albicans,* and 4.0E+03 CFU/cm$^2$ for *Candida aureus.*

In one aspect, a process is provided for fabricating a colorimetric nanofiber biosensor, the process comprising coaxially electrospinning a core material within a shell material to thereby form the colorimetric core-shell nanofiber; controlling alignment of fibers produced to enhance sensitivity to bacterial lipase; wherein, the core material comprises a biocompatible polymer and the shell material comprises a biocompatible polymer, a hemicyanine dye, and a surfactant.

In another aspect, a fabrication process is provided wherein a surfactant is selected from any of Tween10, Tween 40, Tween 60, Tween 80, Triton x100, sodium dodecyl sulfate.

In one aspect, a fabrication process is provided wherein alignment of said core-shell nanofiber is controlled during electrospinning to form a fibrous membrane comprising cross-aligned nanofiber.

In one aspect, a fabrication process is provided wherein said core-shell nanofiber is directed toward a segmented collector during electrospinning.

In another aspect, a biosensor is provided with core-shell nanofibers having a colorimetric probe incorporated in the shell, wherein the colorimetric probe changes color in the presence of pathogens at a specific threshold at or above 1.0E+03 CFU/cm$^2$.

In another aspect, a biosensor is provided wherein a bioactive dye is immobilized at the surface of the shell of core shell nanofibers, and the dye is responsive to the presence of lipase.

In another aspect, a biosensor is provided wherein a bioactive dye is immobilized at the surface of the shell of core shell nanofibers as a colorimetric probe, and the dye is responsive to the presence of lipase, wherein said colorimetric probe changes color from yellow to green when exposed to lipase.

In another aspect, a biosensor is provided with a colorimetric probe that changes color when exposed to any of *Enterococcus faecium, Staphylococcus aureus, Klebsiella pneumoniae, Acinetobacter baumannii, Pseudomonas aeruginosa, Enterobacter species, Escherichia coli, Candida albicans,* and *Candida aureus.*

In another aspect, a biosensor is provided that is usable as a dressing applied to a wound for short-term or longer-term monitoring, and as a point of care assay to detect pathogens present in a fluid extracted from a wound.

A process is described for the preparation of colorimetric nanofiber biosensor comprising: coaxially electrospinning a core material within a shell material to thereby form the colorimetric core-shell nanofiber while controlling alignment of fibers produced to enhance sensitivity to bacterial lipase; wherein: the core material comprises a biocompatible polymer; and the shell material comprises a biocompatible polymer, a hemicyanine dye, and a surfactant such as Tween10, Tween40, Tween 60, Tween 80, Triton x100, sodium dodecyl sulfate or other.

The present invention provides a new approach to improve the detection limit of a biosensor to the presence of pathogens by altering the membranes' physical structure and chemical composition. The present invention has shown that cross-aligned fibers can lead to better localization of bacteria cells. Better localization leads to a higher interaction of dye and bacteria, followed by higher efficacy of dye hydrolysis. Altering the chemical composition of the fiber has been shown to increase lipase activity. Therefore, a higher rate of dye cleavage and an increase in lipase activity paves the path for faster color changing of the biosensor in a lower concentration of bacteria. In addition to providing the physical cues (alignment) for improving bacteria-fibers interaction, in the present invention, a surfactant (e.g. Tween 80) is incorporated in the shell of nanofibers to increase lipase activity.

In the present invention, electrospun membranes are prepared by a modified electrospinning machine to achieve cross-aligned fibers. In addition to providing the physical cues (alignment) for improving bacteria-fibers interaction, a surfactant (e.g. Tween 80) is incorporated in the shell of nanofibers to increase lipase activity. Since lipase is the primarily biomarker for the colorimetric biosensor of the present invention, more active lipase corresponds to higher chance of dye hydrolysis in a lower concentration of bacteria.

The lipases are from the $\alpha$-$\beta$ hydrolase fold proteins family, and their activity depends on the catalytic triad, including Ser, His and ASP. Most lipids have an unstable domain known as the Lid structure. The Lid is an amphipathic structure in which the hydrophilic side faces the solvent in the close conformation while the hydrophobic side is directed toward the triad pocket. Interaction of the Lid with its microenvironment makes the active site accessible for the substrate, known as interfacial activation. In a water-oil interface, the Lid structure changes and activates the lipase; otherwise, the Lid covers the triad most of the time, and the lipase is inactivated. The water-oil interface creates a large hydrophobic patch around the triad, stabling the Lid by the rotations of the Lid around two hinge regions. As the lipase changes its conformation to the open state, the hydrophobic side becomes available and unmasks the substrate-binding region. Therefore, the oil interface presence can help expose the binding domain easily. A surfactant such as Tween 80 can provide this water-oil interface and enhance the Lid unmasking, followed by boosting lipase activity. Hence, in one embodiment of the present invention, in addition to controlling the alignments of fibers, we added Tween 80 in the shell composition to boost the sensitivity of the biosensors.

Till today, a cost-effective, sensitive and fast colorimetric sensor for in situ infection detection has not been developed yet. The present invention decreases the limit of infection detection based on a reliable biomarker (bacterial secreted lipase). We incorporated physical and chemical factors in our design for a nanofibrous colorimetric biosensor. The biosensor can be used for in situ wound infection detection in hospitals (diabetic ulcers, burn, and surgical wounds) and in military/war wounds. This point-of-care biosensor provides a feasible readout for in situ monitoring of the wound condition regarding the infection without the need for ancillary instrumentation or processing. The biosensor of the present invention can provide real-time indications of the presence of pathogens in a wound at a critical threshold of infection. Real-time indications can help stop the progression of bacteria colonization to infection and later on the spread of infection as well as stop unnecessary usage of antibacterial drugs, prevent the mutation of resistant bacteria, and increase the quality of patients' life.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the present disclosure will now be described, by way of example only, with reference to the attached Figures.

FIG. 5 shows color-changing behavior of samples in the presence of different bacteria (Threshold of detection).

FIG. 10 shows interaction of MRSA with different samples after 1 hr of incubation.

DETAILED DESCRIPTION

Figure 1:
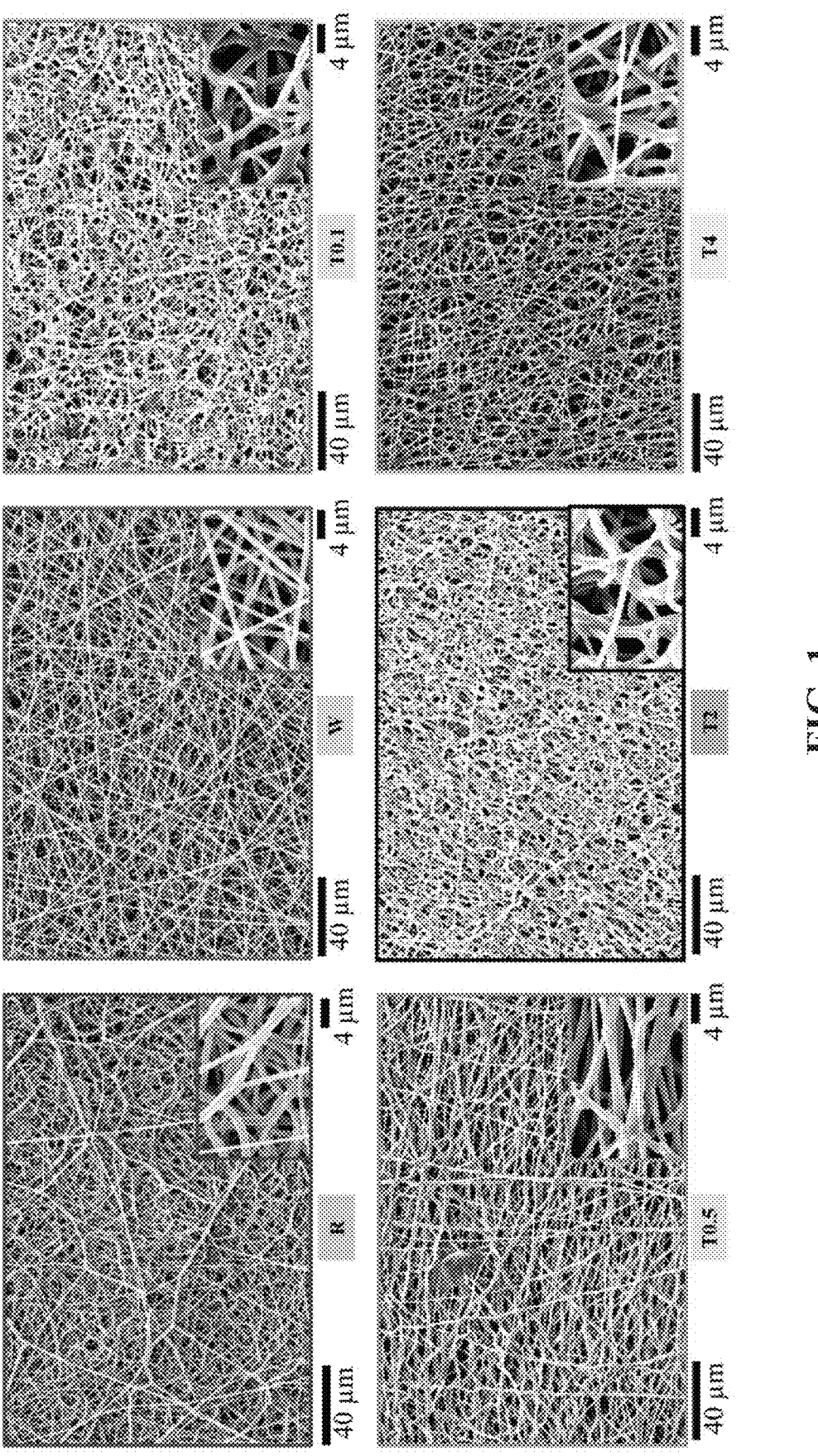
FIG. 1 shows SEM images of different membrane samples with two magnifications (1,000× and 10,000×).

In brief:

FIG. 1 shows SEM images of different membrane samples with two magnifications (1,000× and 10,000×): Random fibers (R), cross-aligned fibers (W), cross-aligned fibers with 0.1% Tween 80 (T0.1), cross-aligned fibers with 0.5% Tween 80 (T0.5), cross-aligned fibers with 2% Tween 80 (T2), cross-aligned fibers with 4% Tween 80 (T4). Each SEM image was used for finding fiber diameter with ImageJ software, and more than 300 diameters were measured.

Figure 1A:
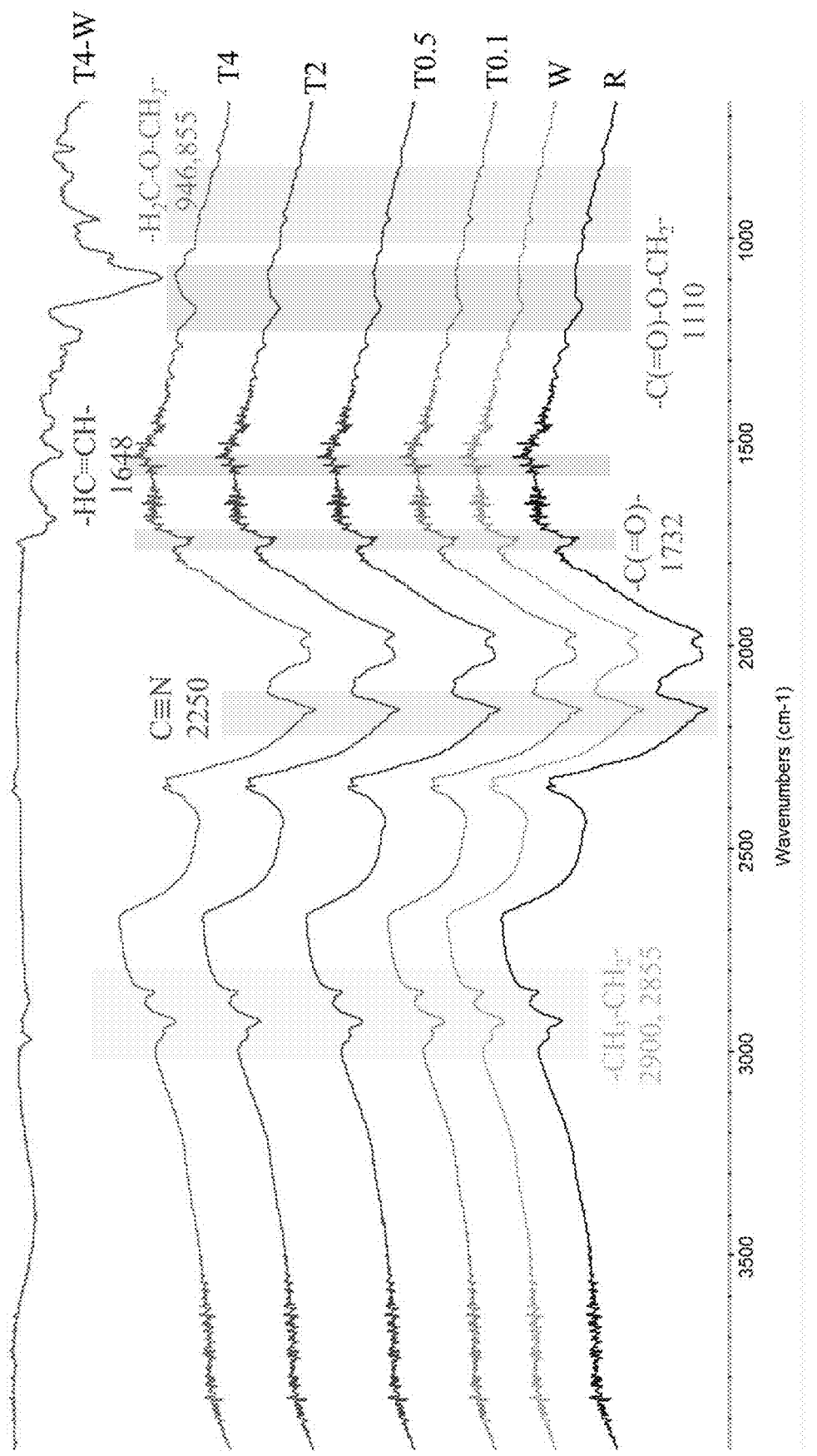
FIG. 1a shows FTIR spectra of membrane of the present invention.

FIG. 1a shows FTIR spectra of membrane: randomly oriented electrospun nanofibres (R), cross-aligned fibers (W), cross-aligned fibers with 0.1% Tween 80 (T0.1), cross-aligned fibers with 0.5% Tween 80 (T0.5), cross-aligned fibers with 2% Tween 80 (T2), cross-aligned fibers with 4% Tween 80 (T4), and subtracted spectra of T4 and W to present the Tween 80 related peaks.

Figure 2:
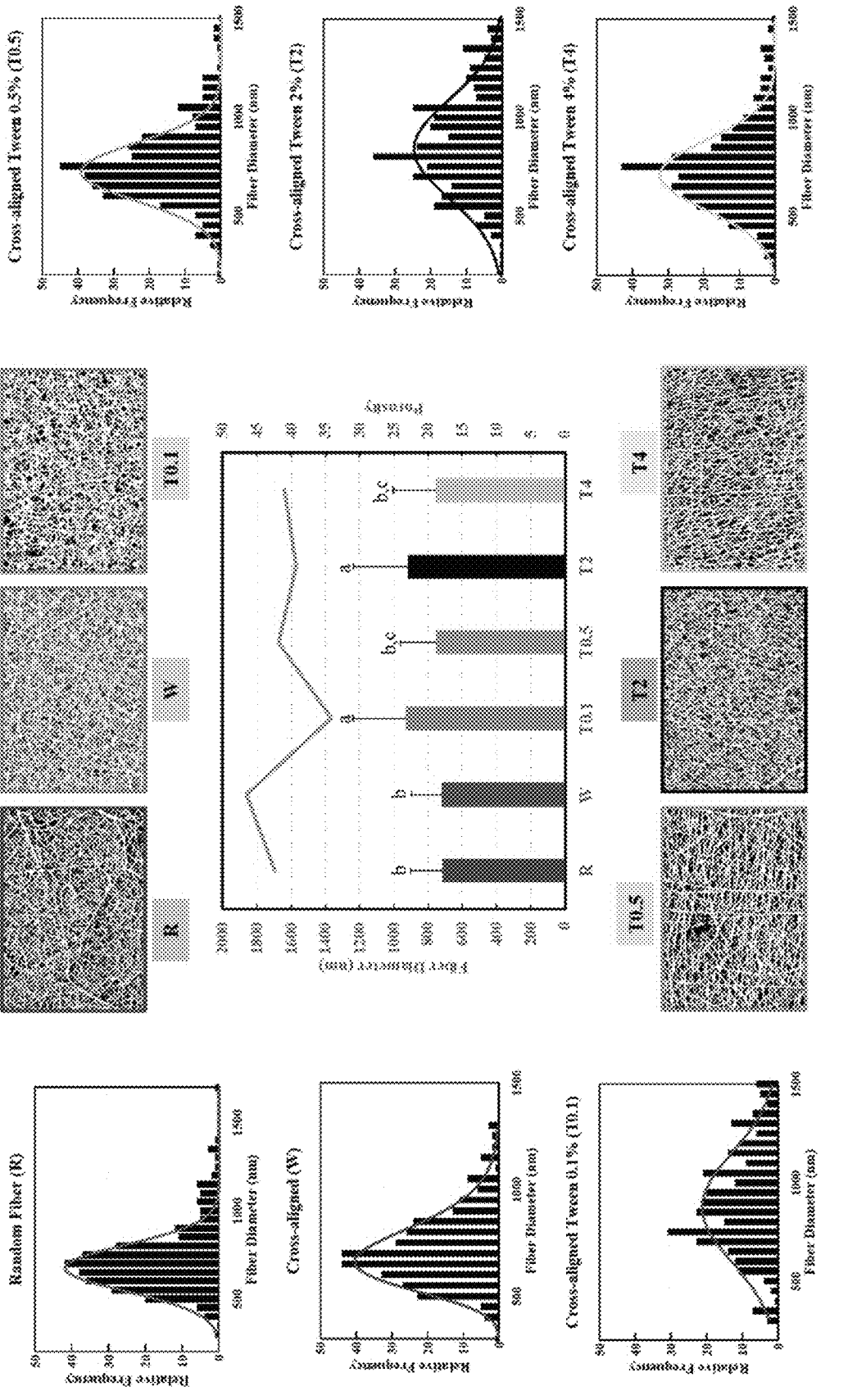
FIG. 2 shows the fiber diameter distribution of different samples in a membrane, mean fiber diameter of each sample, and porosity calculated based on processed images with ImageJ.

FIG. 2 shows the fiber diameter distribution of different samples in a membrane, mean fiber diameter of each sample, and porosity calculated based on processed images with ImageJ. In addition to fiber diameter measurements, SEM images were used to measure the 2D porosity of the fibers. The 2D porosity of fibers, especially the surface layers, plays an essential role in the localization of bacteria. Unlike fiber diameters, the alignment affected the porosity. The addition of Tween 80 suppressed this increase, and the porosity of all samples with Tween 80 remained in the range 34% t-41%.

Figure 3:
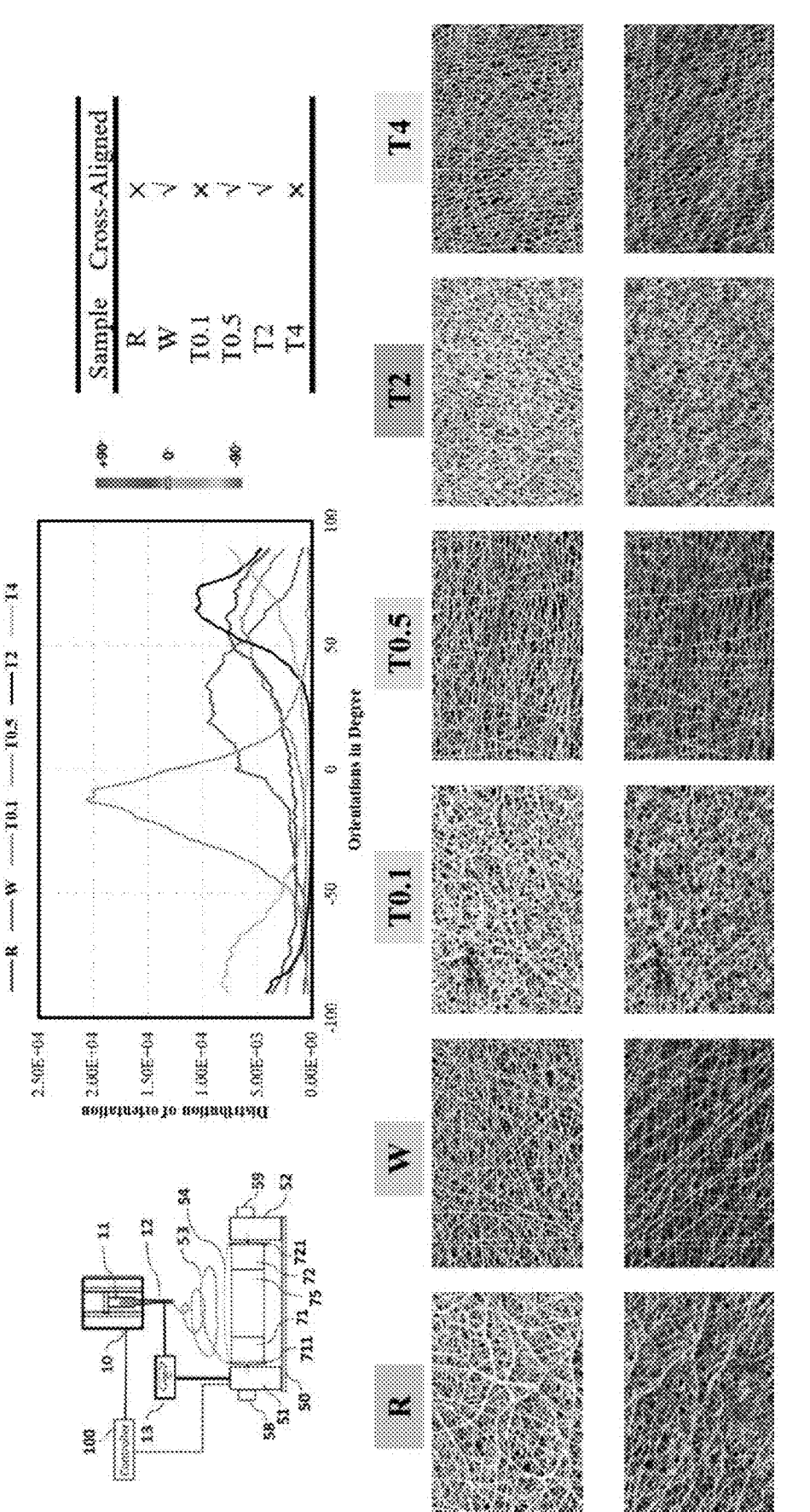
FIG. 3 shows a schematic of the segmented collector for obtaining cross-aligned fibers and color-coded sample maps based on the fibers' orientation.

FIG. 3 shows a schematic of the segmented collector for obtaining cross-aligned fibers and color-coded sample maps based on the fibers' orientation. Each color (hue) represents the degree of orientation. The distribution of orientation for each sample is based on the degree. The less color on the map (monochromatic) demonstrates an aligned structure.

Figure 4:
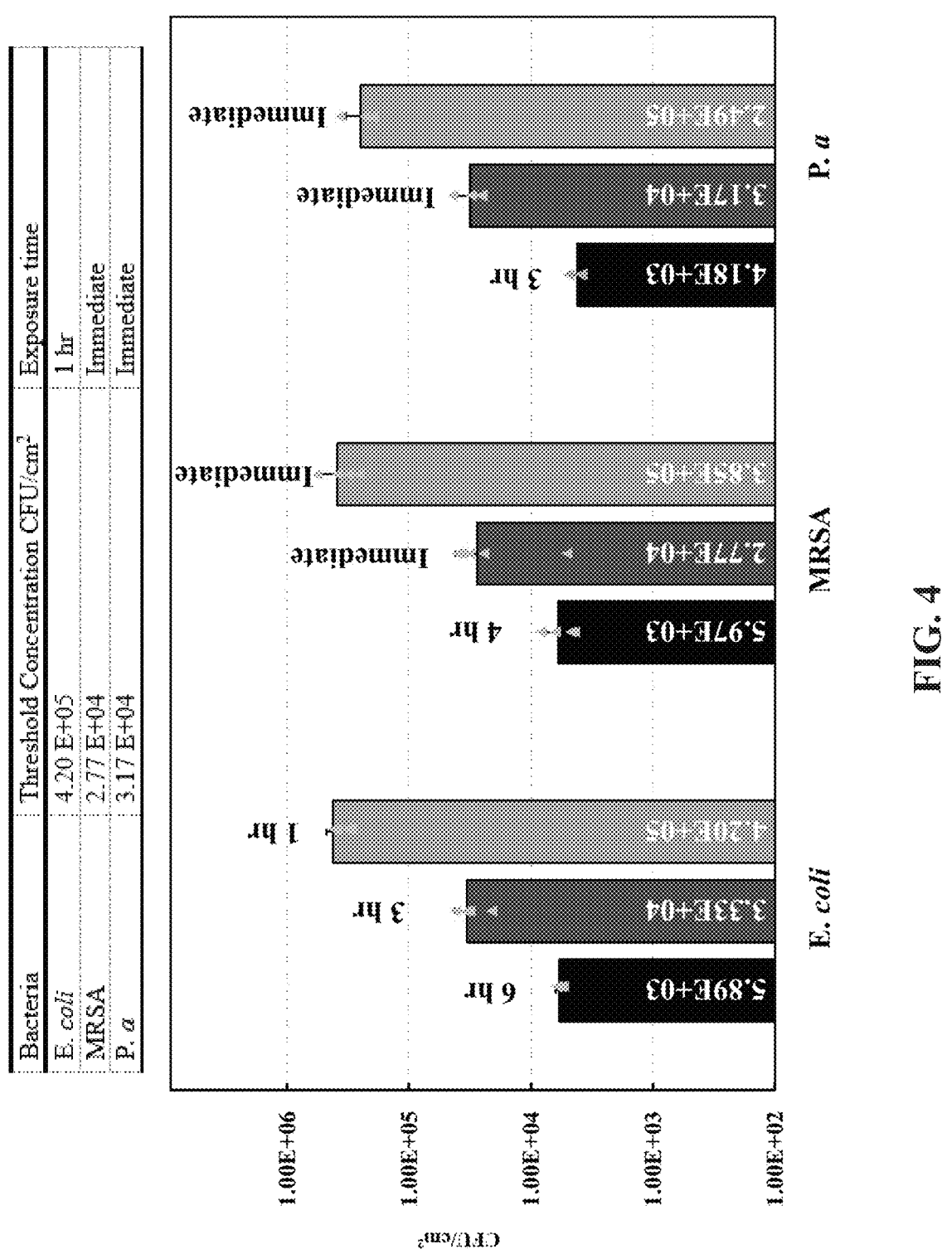
FIG. 4 shows detection threshold for different bacteria and different concentrations of bacteria and exposure time when the first color-changing was observed.

FIG. 4 shows detection threshold for different bacteria. Also shown are different concentrations of bacteria and exposure time when the first color-changing was observed. The addition of the non-ionic surfactant (Tween 80) and preparing cross-aligned fibers were done to boost the sensitivity of bacteria detection and decrease the limit detection compared to our previous research and existing biosensors.

FIG. 5 shows color-changing behavior of samples in the presence of different bacteria (Threshold of detection). All samples with Tween 80 exhibited a faster color-changing compared to W, and among Tween 80 incorporated samples, the membrane containing 0.5% and 2% Tween 80 showed a faster response.

Figure 6:
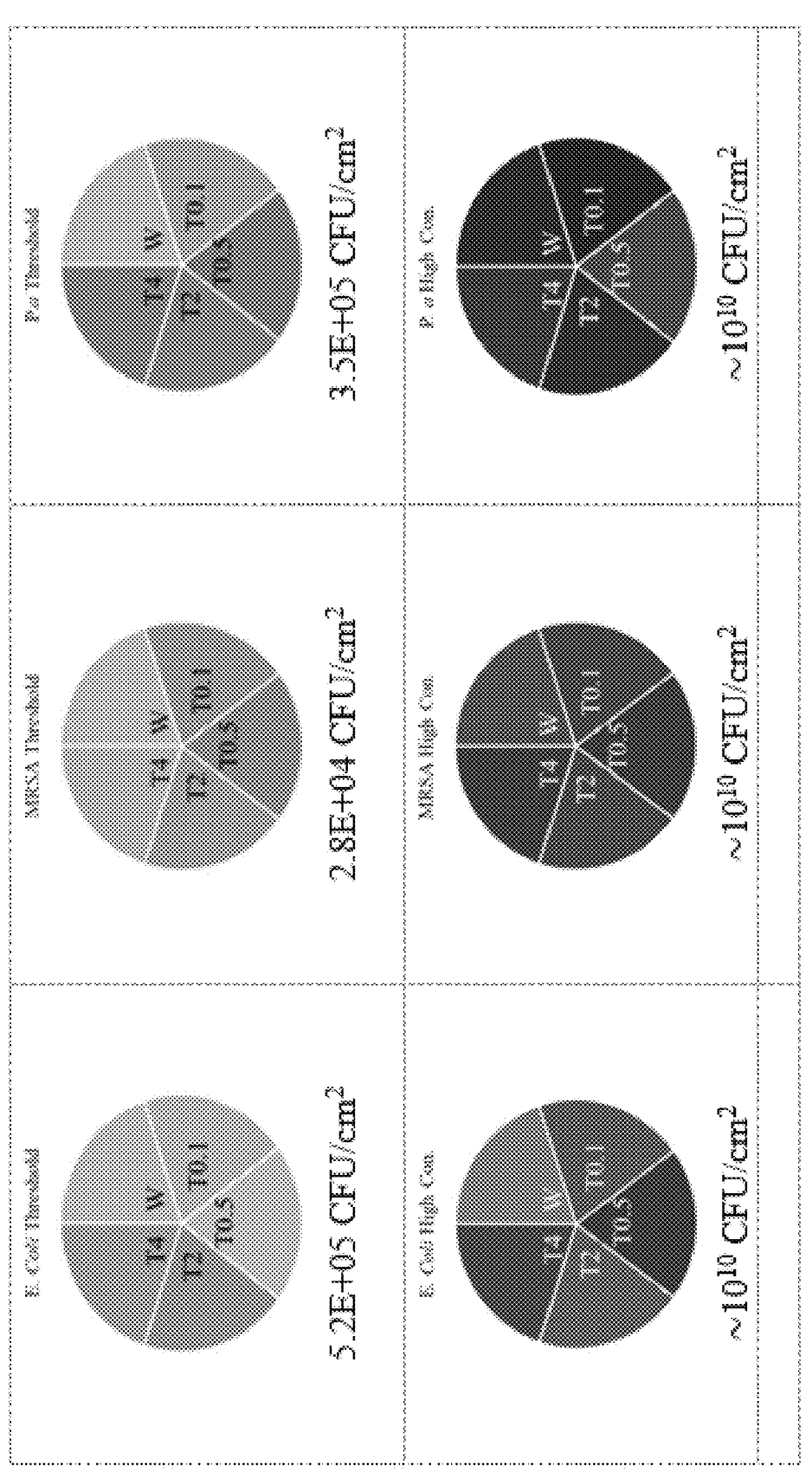
FIG. 6 shows color pallet of biosensors in the presence of different bacteria at a low concentration (limit of detection) compared to the high concentration.

FIG. 6 shows color pallet of biosensors in the presence of different bacteria at a low concentration (limit of detection) compared to the high concentration. The colors of samples at the threshold and high concentrations were quantified based on ΔE and Δh for better comparison. ΔE shows color differences, and it is based on the CMC formula, which is a reliable way to compare colors in the textile industry.

Figure 7:
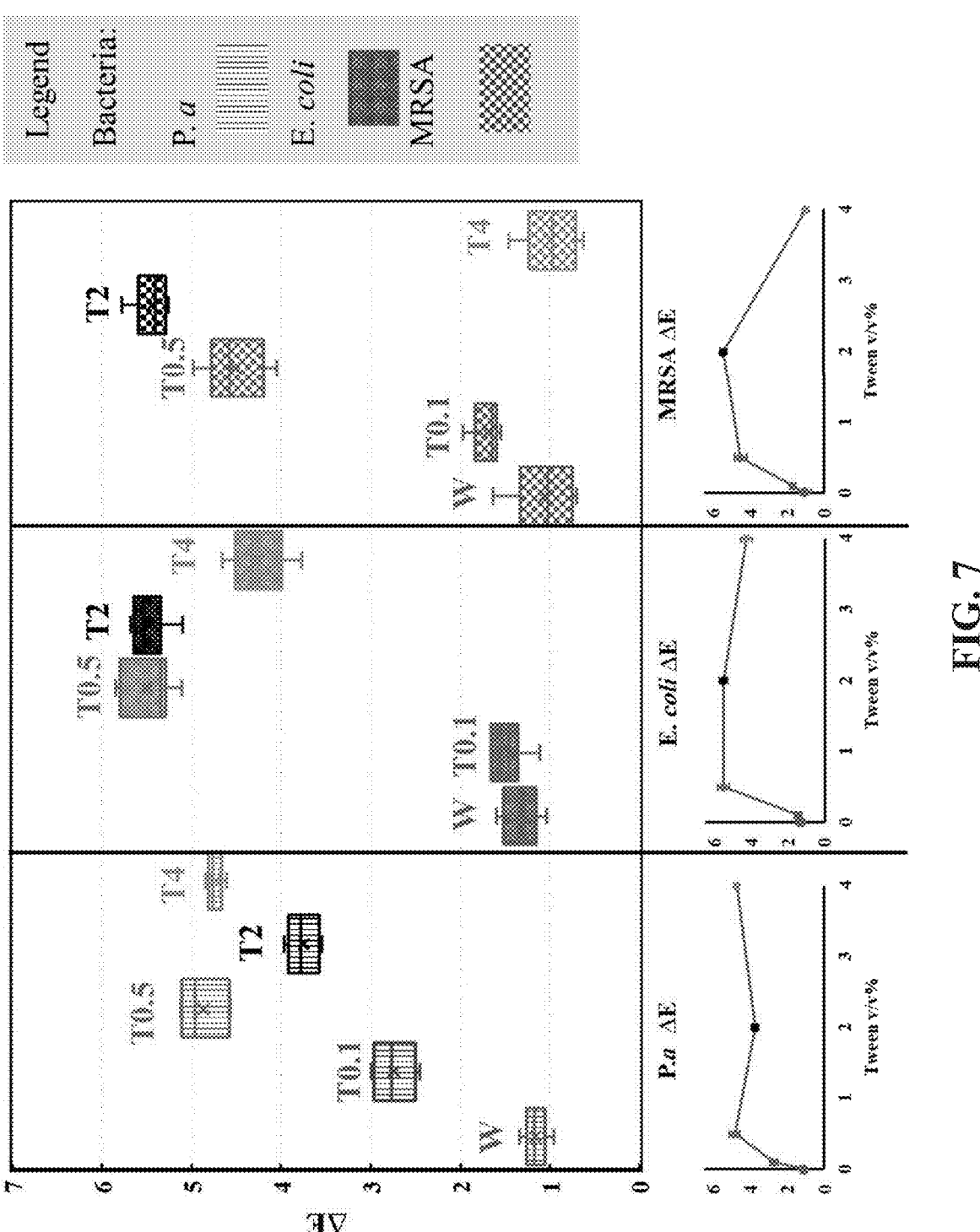
FIG. 7 shows $\Delta E$ of samples in the presence of different bacteria.

FIG. 7 shows ΔE of samples in the presence of different bacteria: the higher ΔE means more distinguishable color differences, and ΔE above 1 can be detected more easily by the human eye. The provided data in FIG. 7 highlights the role of Tween 80 in achieving a faster and noticeable color-changing at a low concentration of bacteria for all used species. The lowest ΔE in the presence of all bacteria is for sample W, which is near 1 and almost no significant changes were detectable by eyes compared to the control sample. The addition of Tween with the lowest concentration (T0.1) increased the ΔE but still, the color difference between the sample and its control (sample on TSA without bacteria) was not considerable, especially for E. coli and MRSA.

Figure 8:
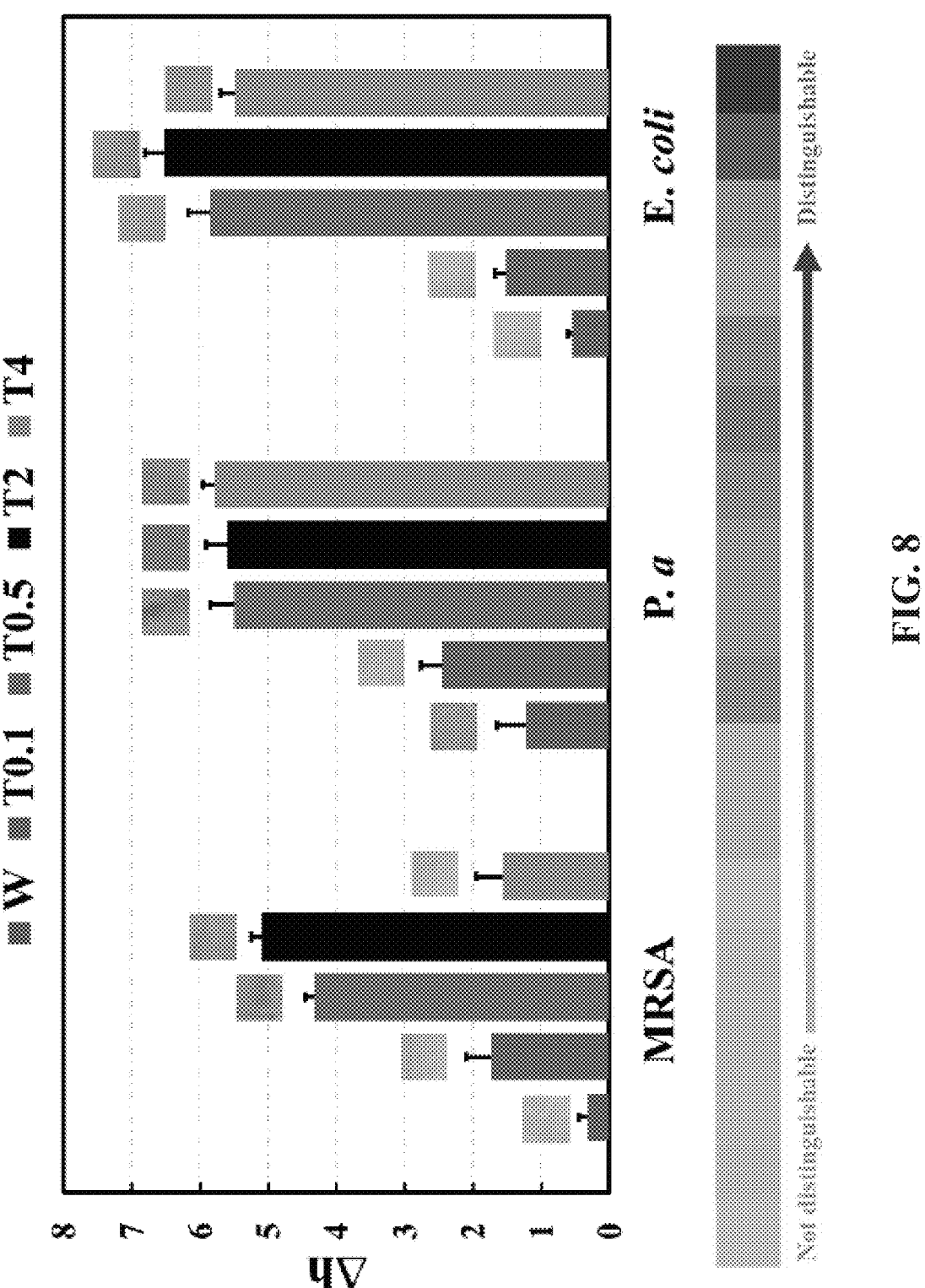
FIG. 8 shows $\Delta h$ (difference in hue) of different samples in the presence of different types of bacteria.

FIG. 8 shows Δh (difference in hue) of different samples in the presence of different types of bacteria. In addition to ΔE (color difference) based on the tolerancing system, the difference in hue (Δh) of samples was quantified to evaluate the color-changing behavior of samples with respect to Tween 80 concentrations. In addition to ΔE (color difference) based on the tolerancing system, the difference in hue (Δh) of samples was quantified to evaluate the color-changing behavior of samples with respect to Tween 80 concentrations. The differences of Δh for the sample without Tween 80 (W) and the sample with the lowest concentration of Tween 80 (T0.1) are significant in all groups of bacteria, and it increases more for the samples with 0.5 and 2% Tween 80.

Figure 9:
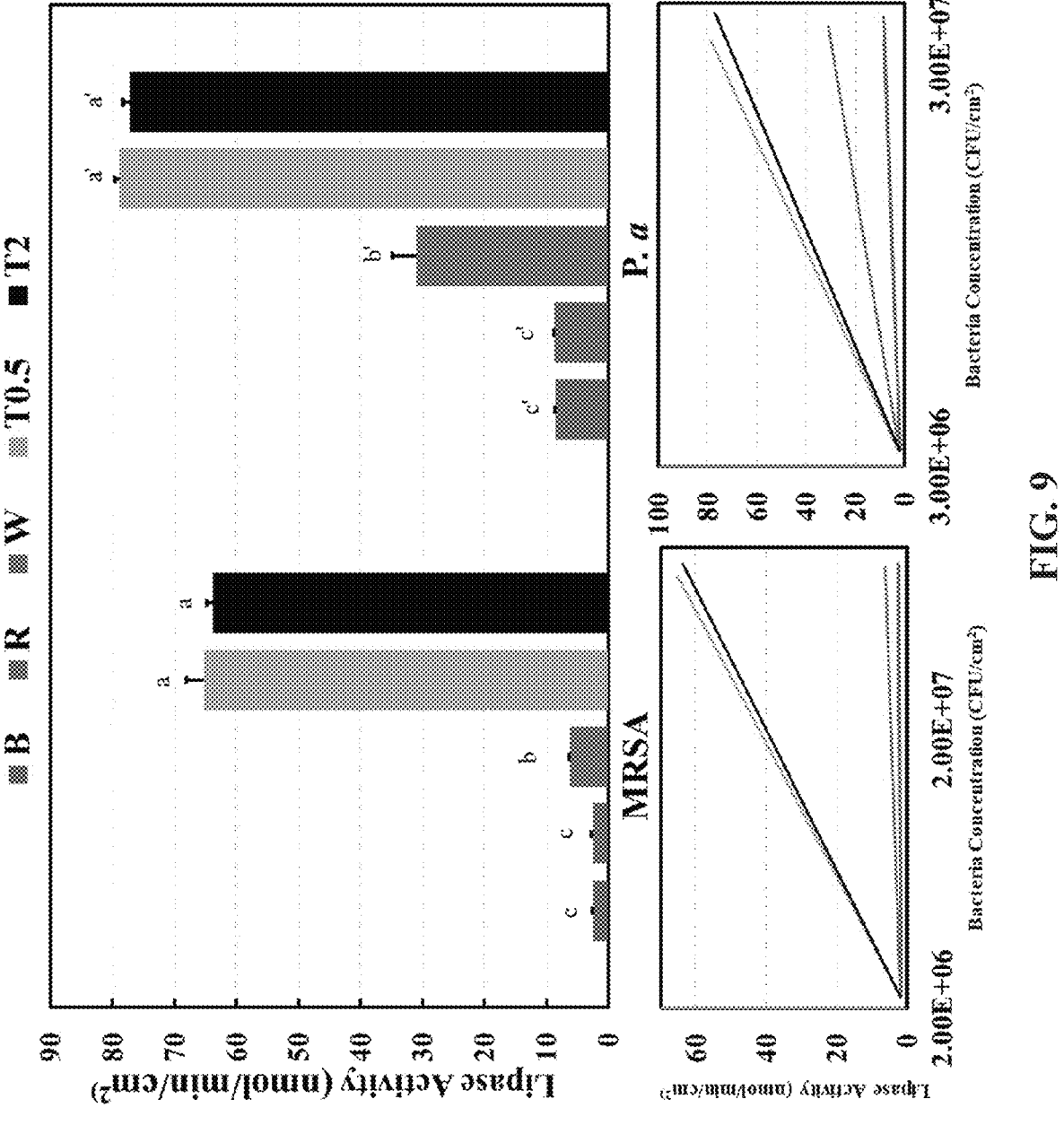
FIG. 9 shows lipase activity of fabricated Biosensors.

FIG. 9 shows lipase activity of fabricated Biosensors: Randomly spun fibers (R), cross-aligned Fibers (W), cross-aligned fibers with 0.5% Tween 80 (T0.5) and cross-aligned fibers with 2% Tween 80 (T2) compare to bacteria without any sample (B). Lipase activity of fabricated Biosensors is presented for randomly spun fibers (R), cross-aligned Fibers (W), cross-aligned fibers with 0.5% Tween 80 (T0.5) and cross-aligned fibers with 2% Tween 80 (T2) compare to bacteria without any sample (B).

FIG. 10 shows interaction of MRSA with different samples after 1 hr of incubation. The bacteria tended to interact with aligned fibers more than random fibers. Also, the presence of Tween 80 led to the agglomeration of bacteria on fibers.

Figure 11:
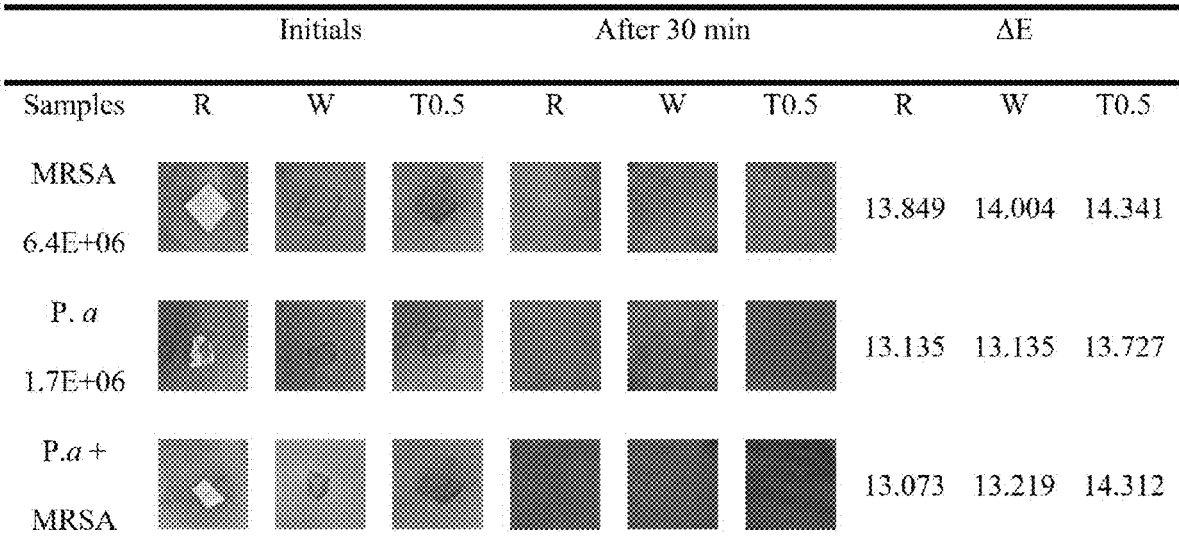
FIG. 11 shows the color-changing response of different samples (randomly spun fiber, cross-aligned sample and Tween 80 incorporated cross-align sample) to the ex-vivo infectious burn wound on a porcine model and the color pallet of samples.
Figure 11:
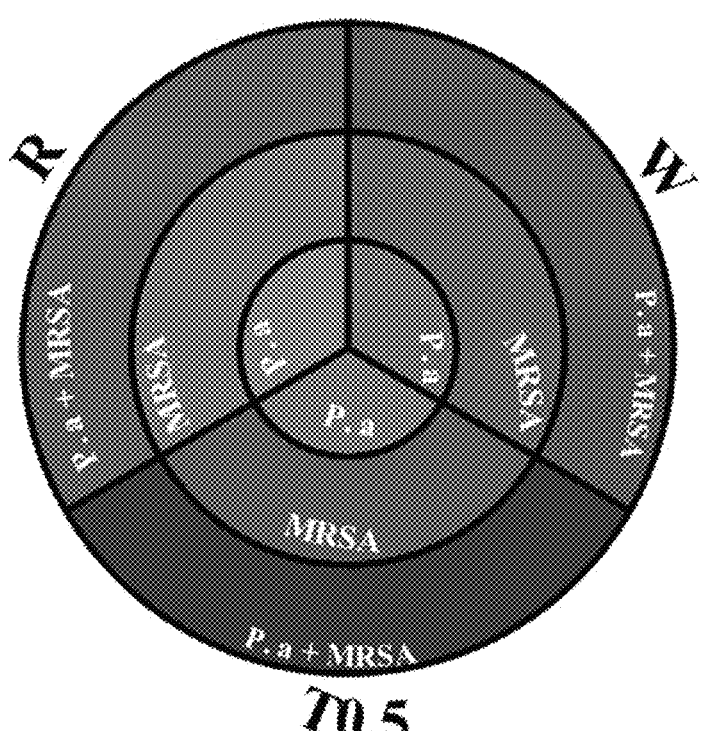

FIG. 11 shows the color-changing response of different samples (randomly spun fiber, cross-aligned sample and Tween 80 incorporated cross-align sample) to the ex-vivo infectious burn wound on a porcine model and the color pallet of samples. The color of the samples became darker within 30 min. for the R sample, the color changing took 30 min. Since the initial concentrations of bacteria were higher than their threshold of detection, all samples showed a color-hanging response.

Figure 12:
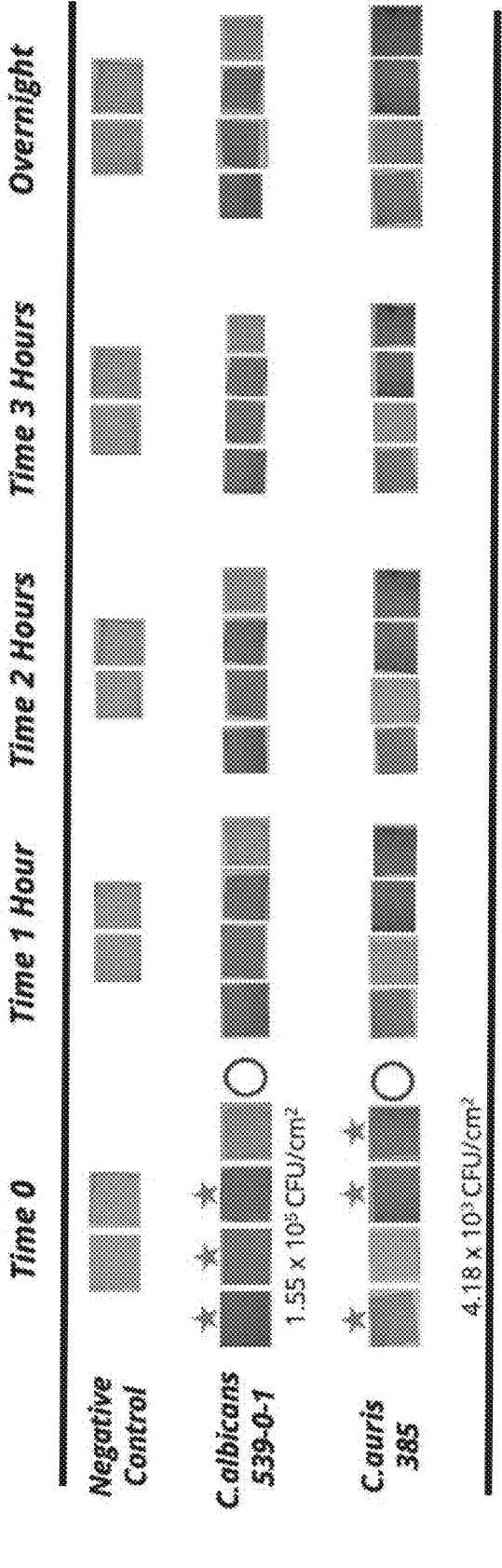
FIG. 12 shows the color-changing response of samples in the presence of two different fungi (Threshold of detection).

FIG. 12 shows the color-changing response of samples in the presence of two different fungi (Threshold of detection). All samples included Tween 80.

Materials and Methods

Materials

Polyvinylpyrrolidone (PVP, Mw 40,000), tetrahydrofuran (THF, ≥99.9%) and N,N-dimethylformamide (DMF, ≥99.8%) were purchased from Sigma Aldrich (St. Louis, MO, USA). Tween® 80, Integra Miltex Standard biopsy punches, BD Bacto™ Tryptic Soy Broth (Soybean-Casein Digest Medium), BD Difco™ Dehydrated Culture Media: Tryptic Soy Agar (Soybean-Casein Digest Agar), 10×PBS Buffer (pH=7.4-0.2 μm filtered) and Aluminum foil were purchased from Fisher Scientific (Nepean, ON, Canada). The Lipase Activity Assay Kit (Colorimetric-ab 10254) was purchased from Abcam Inc. (Toronto, ON, Canada). Teco-philic HP-60D-35 (hydrophilic aliphatic polyurethane, PU) was purchased from Lubrizol Advanced Materials (Cleveland, OH, USA). HCy was synthesized by Alberta Research Inc. (Alberta AB, Canada). MRSA ATCC 33592, P. aeruginosa ATCC 27853, and E. coli ATCC 25922 were obtained from the American Type Culture Collection (ATCC) (Manassas, VA).

Electrospinning Machine for Collecting Cross-Aligned Nanofibers

In order to increase surface contact, reach optimal porosity and enhance bacteria-fibers interaction, a segmented collector was used in a modified electrospinning machine to obtain cross-aligned fibers. The modified electrospinning machine was obtained from Paranano Wound Care LLC. Briefly, the collector comprises first, second, and intermediate segments. The first and second segments are connected to the intermediate segments on opposite ends and work as circumferential conductors at each edge. The first and second segments have electrically chargeable edge conductors, and one edge conductor isolates them electrically from the intermediate segments.

Fabrication of the Biosensor

Six different membranes based on core: shell PU: PU/PVP/HCy nanofibers were prepared with co-axial spinneret apparatus. For core solution, 6% PU was dissolved in DMF:THF 1:1 solution overnight at 45° C., and for shell solutions, 7% PU, 3.5% PVP and 1.01% HCy were dissolved in DMF:THF overnight at 45° C. For samples with the surfactant, the Tween 80 solution was added to the shell solutions and mixed thoroughly. A random fibers membrane and a cross-aligned fibers membrane were prepared based on PU, PVP and HCy without Tween 80 in order to evaluate the role of alignment on the properties of the membrane. Moreover, four membranes with different concentrations of Tween 80 in the shell composition were fabricated to evaluate the role of Tween 80 on different properties, especially lipase activity and sensitivity of the membranes. Overall, 6 samples were prepared as follows: Random fibers without surfactant (R), 2) cross-aligned fibers without surfactant (W), 3) cross-aligned fibers with 0.1% Tween 80, 4) cross-aligned fibers with 0.5% Tween 80, 5) cross-aligned fibers with 2% Tween 80 and 5) cross-aligned fibers with 4% Tween 80. The electrospinning parameters as well as membranes chemical compositions are presented in Table 1.

TABLE 1

Samples compositions and electrospinning parameters.

| | | | Electrospinning parameter | | | | |
|---|---|---|---|---|---|---|---|
| | | Composition | Voltage | Distance | Speed | Flow rate | Interval |
| Name | Core | Shell | kV | cm | rpm | mL/hr | seconds |
| R | 6% PU | 7% PU 3.5% PVP 1.02% Hcy | 19 | 11 | 60 | 1 | NA |
| W | 6% PU | 7% PU 3.5% PVP 1.02% Hcy | 19 | 11 | 60 | 1 | 90 |
| T0.1 | 6% PU | 7% PU 3.5% PVP 1.02% Hcy 0.106% Tween 80 | 19 | 11 | 60 | 1 | 90 |
| T0.5 | 6% PU | 7% PU 3.5% PVP 1.02% Hcy 0.53% Tween 80 | 19 | 11 | 60 | 1 | 90 |
| T2 | 6% PU | 7% PU 3.5% PVP 1.02% Hcy 2.12% Tween 80 | 19 | 11 | 60 | 1 | 90 |
| T4 | 6% PU | 7% PU 3.5% PVP 1.02% Hcy 4.24% Tween 80 | 19 | 11 | 60 | 1 | 90 |

Obtaining the cross-aligned structure in the modified electrospinning machine described above relies on switching the grounding between the barrel and the disks. The spinning time in each state (barrel or disk) before switching is called an interval, and the complete duration of one barrel grounding and one disk grounding is called one layer. If the number of layers exceeds the optimum number, the cross-aligned structure will not be obtained. Therefore, the optimum intervals and layers number were defined as 90 seconds and 20 layers, respectively, to have a cross-aligned structure.

In addition to keeping the optimum number of layers, a non-conductive film should cover the collector to get aligned fibers; otherwise, a conductive film (aluminum film) interferes with grounding, and aligned fibers cannot be obtained.

The following Table (Table 2) presents the amount of Tween 80 used compared to the amount of used dye and polymers for each sample. The ratio of Hcy and Tween 80 is important because Hcy is the chromogenic probe that facilitates the color changing due to lipase, and Tween 80 is the surfactant that increases lipase activity.

TABLE 2

Concentrations of Tween 80 its ratio to main polymers and HCy dye

| Sample name | Tween 80 v/v % | Tween 80 wt % | Tween 80/ polymers | Tween 80/ HCy |
|---|---|---|---|---|
| R | 0 | 0 | 0 | 0 |
| W | 0 | 0 | 0 | 0 |
| T0.1 | 0.1 | 0.106 | 0.06 | 1.04 |
| T0.5 | 0.5 | 0.53 | 0.32 | 5.20 |
| T2 | 2 | 2.12 | 1.28 | 20.78 |
| T4 | 4 | 4.24 | 2.57 | 41.57 |

Chemical Characterization of the Biosensor

Prepared membranes were used for chemical characterization with attenuated total reflectance-Fourier transform infrared (ATR-FTIR, Thermo Scientific, Nicolet is10) to demonstrate the presence of Tween 80 in the structure.

Morphological Characterization of Biosensor

Morphology and alignment of the electrospun nanofibers were characterized using scanning electron microscopy (SEM, FEI Quanta FEG 650). Samples were sputter coated for 45 s with gold-palladium (60:40), and SEM was conducted with an accelerating voltage of 10.0 kV. Fiber diameters were measured from SEM images using ImageJ, and fiber diameter distribution was found based on 300 fiber measurements. The alignment of the membrane was observed from the SEM images with 1,000× magnification. The images were analyzed with the ImageJ-OrientationJ plugin to get a colored map presenting the orientation of fibers in color. After setting the scale of images and finding δ (the mean diameter of fibers in pixel ratio), the SEM images were de-framed. The other parameters, such as coherency and energy, were set at 10%. The final color map shows the direction of fibers, and the hue represents the angle of local fibre orientation (−90° to 90°)

Moreover, the ImageJ particle analyzer was used to find the porosity of membranes. After setting the scale of images and converting them to 8-bit images, the threshold of each image was adjusted to have red color for the background and black for fibers. When all fibers were black, the void area was calculated with the particle analyzer, and the percent of porosity was obtained based on the following equation.

$$\text{Prosity } \% = \left( \frac{\text{void area}}{\text{totall area}} \right) \times 100$$

Bacteria Culture

Two leading bacteria causing wound infection were chosen for bacterial tests in this study, namely MRSA ATCC 33592 (gram-positive), *P. aeruginosa* ATCC 27853 (gram-negative) and antibiotics resistant bacteria named *E. coli* ATCC 25922 (gram-negative. All bacteria solutions were prepared in Tryptic Soy Broth (TSB), and Tryptic Soy Agar (TSA) was used for bacteria inoculation The initial bacteria solutions were prepared by suspending colonies of each species in 2.0 mL 0.01 M PBS to obtain turbidity of 0.5 McFarland (MF). Then each solution was diluted 100× in 0.01 M PBS, and 15 μL of the diluted solution was added to 45.0 mL TSB. The broth solutions were incubated for 18 h at 37° C. with shaking at 140 rpm (reaching $10^8$ CFU/mL).

The overnight solutions were used for preparing bacterial lawns. The solutions were diluted by a factor of 100×, and then 100 μL of diluted solutions were spread on TSA plates and incubated for different time intervals (0, 2, 5 and 12 hr) to reach different concentrations of bacteria.

Limit of Bacteria Detection Via the Biosensor

Bacteria lawns on TSA with different concentrations of bacteria were used to find the threshold of color changing regarding the concentration of bacteria (limit of detection). 1×1 (cm×cm) samples were placed on agar, and digital images were taken initially. The plates were incubated at 37°

C.; every 15 min, the plates were observed for color changing. When the first color-changing was observed, the final digital images were taken, and the concentration of the plate was calculated with a standard drop-plating technique. Briefly, agar plugs were removed from the plates (n=4-6) with Integra Miltex Standard biopsy punches (d=0.4 cm) sonicated for 2 min in 1 mL PBS to detach the bacteria from the surface of the agar. Then 10× serial dilutions were plated drop by drop on the agar plates and incubated for 18 h at 37° C. The number of colonies for each dilution was counted, and the concentration was found based on the following equations.

$$\text{Concentration of Bacteria (CFU/mL)} = \frac{\text{Number of colones}}{\text{USed Volume (mL)} \times 10^{Dilution}}$$

$$\text{Concentration of Bacteria (CFU/cm}^2\text{)} =$$

$$\frac{\text{number of colones extracted from the biopsy (CFU)}}{\pi r^2}$$

Colorimetric Behavior of the Biosensor in the Presence of Bacteria

In addition to taking digital images, the color of biosensors was evaluated with a spectrophotometer (GretagMacbeth ColorEye 2180UV) with L:C 2:1 for the CMC formula to calculate $\Delta E$ and $\Delta h$ (difference in hue) of samples. CF=1 was considered for the $\Delta E$ data.

$$\Delta E = \sqrt{\left(\frac{\Delta L}{lS_L}\right)^2 + \left(\frac{\Delta C}{cS_C}\right)^2 + \left(\frac{\Delta H}{S_H}\right)^2}$$

Where, $$\Delta C = C_1 - C_2 \quad C_1 = \sqrt{a_1^2 + b_1^2} \quad C_2 = \sqrt{a_2^2 + b_2^2}$$

$$\Delta H \sqrt{\Delta a^2 + \Delta b^2 - \Delta c^2} \quad \Delta L = L_1 - L_2$$

$$\Delta a = a_1 - a_2 \quad \Delta b = b_1 - b_2$$

$$S_L = o.511 \text{ if } L_1 < 16 \quad S_L = \frac{0.40975 L_1}{1 + 0.017654 L_1} \text{ if } L_1 \geq 16$$

$$S_c = \frac{0.0638 C_1}{1 + 0.0131 C_1}$$

$$S_H = S_C (FT + 1 - F)$$

$$T = 0.56 + |0.2\cos(H_1 + 168°)| \text{ if } 164° \leq H_1 \leq 345°$$

$$T = 0.36 + |0.4\cos(H_1 + 35°)| \text{ otherwise}$$

$$F = \sqrt{\frac{C_1^4}{C_1^4 + 1900}} \quad sH = \text{Arctan}\left(\frac{b_1}{a_1}\right) \quad H_1 = H \text{ if } H \geq 0$$

$$H_1 = H + 360° \text{ otherwise}$$

In addition to the quantitative data for color-changing, a color pallet was prepared for each bacteria and each membrane at the threshold concentrations and high concentrations that can be used as a reference for the color-changing behavior of the biosensors. It should be noted that for each sample, the data was compared to its own control on an agar plate.

CMC is a common way to compare colors in the textile industry and is a tolerancing system. The provided formula defines an ellipsoid around the standard color that the semi-axis resemble hue, chroma and lightness. For this study, we chose CF=1, which means $\Delta E \geq 1$ corresponds to a significant color change from yellow. In addition to $\Delta E$, the difference in the hue of samples is also reported as an absolute color change, and larger $\Delta h$ presents more decent color-changing.

Effect of Biosensor on Lipase Activity

In order to increase the sensitivity of biosensors, we added a non-ionic surfactant (Tween 80) to the shell structure. The Tween 80 can help to unmask the activation domain by providing an interfacial surface. Therefore, to test our hypothesis, we conducted a lipase activity test. The bacteria plates were prepared as described previously, and after 5 hr of incubation at 37° C., samples were placed on the plates. The initial concentration of each plate was calculated based on biopsied agar plug upon placing the samples, and the final concentration of each plate was calculated based on biopsied agar plug after 3 hr of incubation at 37° C. Regarding the lipase activity, the initial activity was calculated for pre-incubated agar based on biopsied agar plug and the final activity was calculated for bacteria in contact with the collected membranes. The bacteria were separated from the membranes/agar plugs with ultrasonication for 2 min, then centrifuged at 10.000 g for 15 min. 50 µL of each solution was added to a well in a 96-well plate containing assay buffer and reagents. The plate was read with a microplate reader (BioTek-PowerWave XS2) in kinetic mode at 37° C. with readings every 2 min for 1 h. A standard curve was prepared based on the manufacturer's protocol, and the lipase activity was calculated for each sample (n=6).

Interaction of Bacteria and Biosensor (Effect of Alignment on Localization)

The high concentration plate of MRSA (5.2 E+08 CFU/cm²) was used for evaluating the interaction of bacteria and biosensors. Biosensors with 1×1 (cm×cm) dimensions were placed on agar and incubated for 1 hr at 32° C. Then biosensors were collected and immersed in glutaraldehyde solution (0.25%) for the fixation procedure (30 min, room temperature). Then the biosensors were washed with 0.01M PBS three times and immersed in a series of ethanol (30%, 50%, 70%, 80%, 90%, 100%) for 10 min; the 100% solution was changed twice. Then the samples were air dried for 18 hr before analyzing with SEM (FEI Quanta FEG 650). Samples were sputter coated for 45 s with gold-palladium (60:40), and SEM was conducted with an accelerating voltage of 10.0 kV. The SEM images were analyzed with ImageJ software to count the numbers of bacteria and evaluate their interaction with membranes.

Colorimetric Behavior of Biosensors in an Ex-Vivo Burn Model

To evaluate the behavior of biosensors in a more realistic situation, we used the porcine burn model developed in our group's previous studies. Pig skins were cut to 4×4 (cm×cm) prices and were burnt with a heated brass rod (2×2 (cm×cm)-9.2 N) for 1 min, and then the burnt skins were placed in a NaCl (0.9%) solution for 10 min, followed by 70% Ethanol. The skins were air dried and sterilized with UV prior to bacterial inoculation. MRSA and *P. aeruginous* were used to prepare infected wound models by spreading 20 µL of bacteria solutions on the burnt skin. After 2 hr of incubation at 37° C., 1×1 (cm×cm) samples were placed on wounds and the color-changing behavior of biosensors was monitored. A burnt skin without bacteria was used as a control for each sample, and $\Delta E$ was calculated as described before.

Statistical Analysis

All data presented in this study are in mean format±standard deviation, and the number of replications is present as an n-value. In order to compare the data with each other, we used the one-way analysis of variance (ANOVA) with considering a significant difference at p<0.05-95% confidence.

In Detail:

Chemical Characterization of Biosensors

Different membranes based on the primary PU polymer were fabricated by core-shell structure. This study aims to increase the sensitivity of bacteria detection by incorporating Tween 80 in the shell composition as well as controlling fiber alignment. All membranes have PU as their core with 6% concentration and PU:PVP with a 2:1 ratio as their shell. A randomly spun membrane and a cross-aligned membrane only based on PU and PVP were fabricated as controls to evaluate the role of alignment. Moreover, different membranes with different concentrations of Tween 80 from 0% to 4% were prepared to investigate the role of the surfactant in boosting sensitivity.

The chemical composition of different membranes was characterized by ATR-FTIR. The main peaks are presented in FIG. 1. The spectra of the aligned membrane and membranes containing Tween 80 were subtracted from each other (T4-W) to evaluate the presence of Tween 80 in the membranes. The absence of the peak related to the C≡N stretch at 2250 cm−1 demonstrated that the subtracting happened successfully since this peak is related to the HCy dye and should have the same intensity in both samples. The remaining peaks are peaks related to Tween 80, including —H2C—O—CH2- (946 cm−1), —CO—O—CH2- (1100 cm−1), —CH2-CH3 (2855 cm−1 and 2900 cm−1), and C═O stretch at 1732 cm−1 [38]. These peaks demonstrate that Tween 80 was successfully incorporated into the shell of nanofibers without any chemical interaction with other polymers or the dye.

Morphological Characterization of Biosensors

Referring to FIG. 1, the SEM images of samples were taken with different magnifications to evaluate the fiber diameter and alignment of the fibers. FIG. 1 presents the SEM images of samples (R. W. T0.1. T0.5, T2 and T4) with two magnifications (1,000× and 10,000×): Random fibers (R), cross-aligned fibers (W), cross-aligned fibers with 0.1% Tween 80 (T0.1), cross-aligned fibers with 0.5% Tween 80 (T0.5), cross-aligned fibers with 2% Tween 80 (T2), cross-aligned fibers with 4% Tween 80 (T4). Each SEM image was used for finding fiber diameter with ImageJ software, and more than 300 diameters were measured.

Referring to FIG. 1a, FTIR spectra of membrane of the present invention is shown for randomly oriented electrospun nanofibres (R), cross-aligned fibers (W), cross-aligned fibers with 0.1% Tween 80 (T0.1), cross-aligned fibers with 0.5% Tween 80 (T0.5), cross-aligned fibers with 2% Tween 80 (T2), cross-aligned fibers with 4% Tween 80 (T4), and subtracted spectra of T4 and W to present the Tween 80 related peaks.

Based on the means of fiber diameter for samples R and W, it can be said that controlling the alignment of the fibers by changing the grounding of the collector from the disk to the barrel or vice versa after every 90 seconds to get 20 layers did not affect the diameter. Randomly spun fibers (R) and cross-aligned spun fibers (w) have almost the same fiber diameter range with a similar distribution, 718±184 and 720±177 μm, respectively. On the other hand, the addition of Tween 80 in the polymer solutions for electrospinning (0.1, 0.5, 2 and 4 v/v %) in the shell affected both the size and distribution of fibres (uniformity)—which is aligned with other reports [39]. Interestingly, adding Tween 80 with 0.1 v/v % increased the fiber diameter (932±307 μm) with a wide fibre diameter distribution. Since the concentration of Tween 80 in the T0.1 sample (0.1 v/v %, 7.6E−7.0 M) is lower than the CMC of Tween 80 (1.1E−5.0 M [40]), it cannot affect the surface tension significantly, but the presence of it in the solution caused a larger droplet formation (the feeding rate and voltage were kept constant for all samples) which led to the larger diameter fibres collected. By increasing the concentration of Tween 80 to 0.5%, the surface tension could be lower than the T0.1 sample due to the formation of some micelles; therefore, the mean fiber diameter is significantly smaller (757±204 μm) than T0.1 but almost in the same range as W, and R. Regarding the fiber distribution, increasing the Tween 80 concentration led to collecting more uniform fibres with a narrower fiber distribution compared to T0.1. Increasing the concentration to 2% again caused the same phenomenon as T0.1, an increase in fiber diameter and distribution (919±317 μm). However, the diameter decreased to the initial size (757±245 μm) again by adding more Tween 80 (4%). This fluctuation can be related to having two solvents in the solutions, one polar and the other non-polar. Tween 80 tends to form a hydrophobic core in polar solvents, while a reverse micelle with a hydrophilic core would form in non-polar solvents [41]. Therefore, based on the distribution of Tween 80 in these two solvents and their saturation point, different behavior (fiber diameter and distribution) were obtained.

Referring to FIG. 2, the mean fiber diameter distribution of each sample is presented: fiber diameter distribution of different samples, mean fiber diameter of each sample, and porosity calculated based on processed images with ImageJ. In addition to fiber diameter measurements, SEM images were used to measure the 2D porosity of the fibers. The 2D porosity of fibers, especially the surface layers, plays an essential role in the localization of bacteria. The 2D porosity was measured with ImageJ software by changing the images' threshold to separate the fibres from empty spaces. Based on the obtained result (FIG. 3), the 2D porosities of different membranes are almost in the same range (42%-R, 46%-W, 41%-T0.5, 39% T2 and 40% T4), and only the lowest concentration Tween 80 (T0.1) showed a noticeable decrease to 34%.

Moreover, to the porosity and fiber diameter, the SEM images were used to determine whether controlling the fiber alignment was successful or not. The SEM images were pre-analyzed and unframed, and the size of the area of interest (ROS) was defined. Then with the ImageJ plugin (OrientationJ), each image was analyzed to get a color-coded map that hue corresponds to the degree of alignment. If getting cross-aligned fibers was successful for each sample, only two monochromic colors should be present on the map (crossing with 90°). FIG. 3 shows a schematic of the designed collector for collecting cross-aligned fibers and color coded map as well as a distribution graph of orientation for different samples.

Referring to FIG. 3, a non-limiting schematic of the segmented collector for obtaining cross-aligned fibers is presented, along with color-coded sample maps based on the fibers' orientation. Each color (hue) represents the degree of orientation. And the distribution of orientation for each sample is based on the degree. The less color on the map (monochromatic colors) demonstrates having an aligned structure. If the cross-aligned fibers are obtained, they should have monochromatic color on their map. Sample W, which is only based on polymers and dye without Tween 80, maintained its alignment and a cross-aligned structure was observed. The map contains two dominant colors in the range blue (0°) and pink (90°), showing 90° differences, hence the cross-aligned structure. But, adding Tween 80 with the lowest concentration (T0.1) interfered with the alignment, and random fibers were collected; additionally, instead of straight fibers, curly fibers were obtained. However, increasing the Tween 80 concentration to 0.5% helped keep the alignment and fibers structure. Although the dominant colors for T0.5 are not the same as W, the difference between the degrees of the two dominant colors, green and blue (−50° to 40°), is still 90°. Therefore, the cross-aligned structure is also present in this sample. The T2 sample is also aligned based on color coding, but the fibers are curly, making it hard to observe the alignment. Moreover, the angle between fibers is less than 90° since colors are in the range of purple and pink (50°-90°). Increasing Tween 80 to 4% led to complete randomness in fiber collection, and almost all colors are present on the map. The interaction of Tween 80 with ingredients in the solution, its CMC and its effect on solutions properties such as conductivity and viscosity could determine the structure of the fibers.

Referring to FIG. 4, the thresholds of bacteria detection for samples containing Tween 80 (especially T0.5 and T2) are presented. FIG. 4 depicts the detection threshold for different bacteria and different concentrations of bacteria and exposure time when the first color-changing was observed. The addition of the non-ionic surfactant (Tween 80) and preparing cross-aligned fibers in this study were done to boost the sensitivity of bacteria detection and decrease the limit detection compared to our previous studies and existing biosensors. It has been proven that surfactants such as Tween 80 increase the water-lipid interfacial area and lead to a higher reaction rate for lipase. And since lipase is the main contributor to the color-changing of our biosensors, we aimed to increase their activity by incorporating Tween 80 in the structure of the biosensors. Our previous study showed that doping the fibers with PVP could reduce the detection limit to 2 hr after exposure to 2.5 E+05 and 1.0E+06 for *P. a* and MRSA, respectively. Herein, sensitivity is increased by reducing the time of detection and concentration of bacteria.

To test the detection limit, we prepared different concentrations of three main bacteria responsible for wound infection, namely *E. coli, P. a* and MRSA. Different concentrations of bacteria were prepared by pre-incubation of bacteria lawn at 37° C. for different intervals. After the pre-incubation, the biosensors were placed on the bacteria lawns, incubated at 32° C. and monitored for color changes every 15 minutes. The concentration of each plate was measured right after pre-incubation, and the required time for color-changing was recorded. FIG. 4 illustrates the concentrations and duration of the first color-changing.

At a low concentration of bacteria, around 4.0-6.0E+03 CFU/cm$^2$ in all species (*E. coli*, MRSA and *P. a*), the first color-changing took a long time to be detected: *E. coli* 6 hr. MRSA 4 hr and *P. a* 3 hr. But increasing the concentration of MRSA and *P. aeruginosa* by less than one log (around 3.0E+4.0 CFU/cm$^2$), below the clinical detection threshold (5.0E+04−4.6E+05 CFU/cm$^2$), led to immediate changes for samples containing Tween 80. It should be mentioned that the behavior of samples with different Tween 80 concentrations was different, and T0.5 and T2 showed the fastest and most vivid color-changing for all bacteria. For *E. coli*, the presence of Tween 80 had an effect, but it was not as significant as other species. For *E. coli* at a concentration around 3.3E+04 CFU/cm$^2$, it took 3 hr for Tween 80 incorporated samples to change their color, while for the W sample time was more (5 hr). by increasing the concentration of *E. coli* (4.20E+05 CFU/cm$^2$) we were able to get the color-changing after 1 hr of exposure. Therefore the thresholds of bacteria detection for samples containing Tween 80 (especially T0.5 and T2) are as presented in FIG. 4.

Referring to FIG. 5, samples are shown that changed color in the presence of each bacteria at the detection threshold. All samples with Tween 80 showed a faster color-changing compared to W, and among Tween 80 incorporated samples, the membrane containing 0.5% and 2% Tween 80 showed a faster response. Therefore, the reported time for each bacteria regarding the color-changing is for the first sample that changes its color. Interestingly, different bacteria showed a different response to the presence of Tween 80 and its concentration. For instance, the high Tween 80 (4%) concentration did not lead to a fast color change for MRSA. However, it facilitated faster color-changing for *P. aeruginosa*

Overall, based on the behavior of the sample in the presence of different bacteria types, the low concentration of Tween 80 (T0.1) increased the sensitivity and color changing from yellow to green happened faster than W; however, the changed color is not strong enough for reliable detection. It can be said that the Tween 80 with 0.1% concentration could not increase the lipase activity significantly, and enough active lipase was not present on the site to lead to a vivid color-changing. Increasing the Tween 80 concentration to 0.5% and 2% led to noticeable color changes from yellow to green which can be observed with untrained eyes for all bacteria types. Therefore, it can be said that the optimal concentration of Tween 80 for reaching the highest lipase activity is in the range of 0.5-2%. Increasing the concentration to Tween 80 to 4% did not change the quality or speed of color changing for samples exposed to *E. coli* and *P. a* compared to T0.5 and T2, but it adversely affected the sensitivity in the presence of MRSA. It can be related to the fact that each bacteria type reacts differently to the presence of surfactants, specifically Tween 80. If Tween 80 concentration passes the optimal (critical) concentration, it inhibits the lipase secretion instead of increasing it, leading to lower activity. The lipase activity inhibition occurs due to strong hydrogen bonds and hydrophobic forces between Tween 80 and enzymes that denatures the lipase. A lower activity of Tween 80 correlates to a less cleaved ester bond of the dye.

A mixed microenvironment of different bacteria with a high concentration was prepared to show the color-changing behavior of all samples in a multi-species situation. As presented in FIG. 5, dark green was obtained for samples T0.5 and T2, but the color for T4 was a bit lighter. The presence of Tween 80 with its lowest concentration (T0.1) affected the lightness of the green color, and it is even lighter than the W. based on the obtained result, the best two samples are T0.5 and T2; these two samples not only have the optimum concentration of the Tween 80 but also have cross-aligned structure.

Referring to FIG. 6, a non-limiting diagram shows the color pallet of biosensors in the presence of different bacteria at a low concentration (limit of detection) compared to the high concentration. In addition to taking digital images of biosensors to evaluate their color-changing, we used the GretagMacbeth ColorEye 2180UV spectrophotometer to quantify the color changes. The colors of samples at the threshold and high concentrations are illustrated in FIG. 6; these colors were quantified based on $\Delta E$ and $\Delta h$ for better comparison. $\Delta E$ shows color differences, and it is based on the CMC formula, which is a reliable way to compare colors in the textile industry. For this project, we chose lightness: chroma 2:1 since human eyes distinguish differences in lightness more than chroma. Moreover, the commercial factor of tolerance (CF) was set to 1, which means the $\Delta E$ larger than 1 corresponds to a color-changing that human eyes can distinguish.

Referring to FIG. 7, the $\Delta E$ of samples are shown exposed to different bacteria at their threshold of color changing. The provided data in FIG. 7 highlights the role of Tween 80 in achieving a faster and noticeable color-changing at a low concentration of bacteria for all used species. The lowest $\Delta E$ in the presence of all bacteria is for sample W, which is near 1 and almost no significant changes were detectable by eyes compared to the control sample. The addition of Tween with the lowest concentration (T0.1) increased the $\Delta E$ but still, the color difference between the sample and its control (sample on TSA without bacteria) was not considerable, especially for *E. coli* and MRSA. For all types of bacteria tested, T0.5 and T2 displayed the most distinct color changes, thus resulting in the highest $\Delta E$. These results are consistent with those reported in the threshold finding data and support the hypothesis that Tween 80 incorporation and maintaining alignment of nanofibers can increase the color difference in a lower concentration of bacteria, thus enhancing the detection limit. As discussed previously, the effect of Tween 80 on lipase activity highly depends on its concentration and type of bacteria; therefore, increasing the concentration to 4% not only could not enhance the $\Delta E$ (color differences) in the presence of tested bacteria but also decrease it significantly mainly for MRSA. There can be a rational explanation for this decrease as Tween 80 interacts highly with lipases (strong hydrogen bonds) that may denature the fourth structure of the lipase, preventing it from attaching to the substrate (the HCy dye) and cleaving it. Therefore, without active lipase and less cleavage, less color changing happened. When it comes to the color change detected with the naked eye with Tween 80, the best results are found with T0.5 and T2.

Referring to FIG. 8 the role of Tween 80 concerning color-changing behavior is highlighted. In addition to $\Delta E$ (color difference) based on the tolerancing system, the difference in hue ($\Delta h$) of samples was quantified to evaluate the color-changing behavior of samples with respect to Tween 80 concentrations. The differences of $\Delta h$ for the sample without Tween 80 (W) and the sample with the lowest concentration of Tween 80 (T0.1) are significant in all groups of bacteria, and it increases more for the samples with 0.5 and 2% Tween 80. However, the differences between T0.5 and T2 are insignificant, and these two concentrations enhanced the color-changing ability at the same level. Align with $\Delta E$ results, increasing the concentration to 4% did not boost the behavior further; notably, the high concentration of Tween 80 reduced the $\Delta h$ significantly for MRSA. Both $\Delta E$ and $\Delta h$ results point to the importance of having the optimum concentration of Tween 80 for boosting the sensitivity of biosensors. Since the aim is to detect multi-species of bacteria, the optimum concentration should lead to a noticeable color-changing for different types of bacteria. In this case, T0.5 and T2 are chosen as the optimum concentrations for their exemplary behavior of color-changing and for having cross-align structures.

Tween 80 was chosen as an additive in the biosensors compositions to enhance the sensitivity of biosensors for two main reasons. Firstly, to provide a large interfacial area between lipase and the dye (substrate) and secondly, as an activator of lipase. Overall, both roles should result in higher activation of lipase in the presence of Tween 80. In addition to incorporating Tween 80, we hypothesized that the nanofibers' alignment could also boost the sensitivity. Therefore, a lipase activity assay was conducted to test lipase activity in the presence of four different membranes, and the results are compared to bacteria without any sample (B). A randomly spun membrane (R), a cross-aligned membrane without Tween 80 (W), and cross-aligned membranes with optimum concentrations of Tween 80 (T0.5 and T2).

Referring to FIG. 9, the obtained results of lipase activity as well as the relation between lipase activity and the bacteria concentrations are illustrated. Lipase activity of fabricated Biosensors is presented for randomly spun fibers (R), cross-aligned Fibers (W), cross-aligned fibers with 0.5% Tween 80 (T0.5) and cross-aligned fibers with 2% Tween 80 (T2) compare to bacteria without any sample (B).

To ensure that the concentration of bacteria does not affect the lipase activity, we prepared all bacteria lawns with the same solution and incubated them for the exact amount of time. Moreover, the initial and final bacteria concentrations for each sample were calculated, and as shown in FIG. 9, all samples are almost equal in terms of their bacteria concentrations. Therefore, comparing lipase activity in the presence of membranes is independent of environmental parameters and the concentration of bacteria. The obtained data supports our hypothesis that better localization of bacteria follows a higher rate of lipase activity. The randomly spun membrane (R) did not change the lipase activity significantly compared to bacteria alone (B), but the cross-aligned membrane increased the activity 3 folds and 4 folds for MRSA and *P. a*, respectively. As we expected, the presence of Tween 80 elevates the lipase activity drastically by 10 folds for MRSA and 2.5 folds for *P. aeruoginosa* compared to aligned samples. However, the activity in the presence of T0.5 and T2 was almost the same. Therefore, the optimum concentration is 0.5%, and the excess amount of Tween 80 higher than 0.5% will not enhance the lipase activity.

Referring to FIG. 10, the interaction of MRSA with different samples is shown after 1 hr of incubation. The bacteria tended to interact with aligned fibers more than random fibers. Also, the presence of Tween 80 led to the agglomeration of bacteria on fibers. To further investigate the role of alignment on the bacteria interaction with samples, we evaluated the morphology of bacteria exposed to the different membranes. Randomly spun (R), cross-aligned (W) and cross-aligned with 0.5% Tween 80 (T0.5) were placed on a high concentration of MRSA bacteria lawn for 1 hour and then were fixed for analysis with SEM. The concentration of bacteria lawns was calculated before applying the membranes with the drop-plating technique and after 1 hour of exposure with ImageJ analysis. The SEM images of samples are presented in FIG. 10, which shows the tendency of bacteria to attach to the cross-aligned sample compared to the R sample. Moreover, the presence of Tween 80 in the structure (T0.5) led to the agglomeration of bacteria on fibers. It seems that where Tween 80 clumps presented, the bacteria tended to interact with the fibers more. These findings also align with the colorimetric results as well as the lipase activity results. Overall, we can claim that the alignment and Tween 80 led to an increase in the sensitivity of the biosensor, and we could reduce the concentration and time of detection from 2 hr exposure to $1.0E+06$ $CFU/cm^2$ and $2.5E+05$ $CFU/cm^2$ for MRSA and *P. aeruoginosa* to $2.8E+04$ $CFU/cm^2$ and $3.2E+04$ $CFU/cm^2$.

Referring to FIG. 11, the colorimetric behavior of biosensors in an ex-vivo burn model is presented. The responsibility of membranes to a realistic situation was evaluated using a porcine burn model. The burn wounds were infected with MRSA and *P. a* separately and mixed. The membranes were placed on skins after one hour of incubation, and the bacteria concentration was calculated initially.

As presented, both W and T0.5 samples had an initial and immediate colour-changing response upon placing on the burnt skin and continued to become darker as time passed. For the R sample, no initial and immediate colour-changing was observed; the colour-changing took 30 minutes. Since initial concentrations of bacteria were higher than their threshold of detection, all samples showed a color-hanging response. But the point is that the Tween 80 incorporated cross-aligned sample not only showed the fastest change but also had the darker initial response, making it easier to observe care with the naked eye. After 30 minutes, all membranes were sandwiched between two glass slides and used for colorimetric analysis with the spectrophotometer. All samples showed a high color difference ($\Delta E$) compared to the control, and the highest $\Delta E$ was for the T0.5 sample.

Although responding to a high concentration of bacteria ($\sim$1.0–6.0E+06) may not be applicable for clinical application in hospitals in developed countries, it can save lives during wars and battles or even after wars in conflict situations such as refugee camps where access to laboratories is limited [48]. The gold standard for infection detection is biopsy or swabbing bacterial culture. In addition to being invasive and requiring wound dressing removal to get the results, these techniques need a 24 hr. incubation time. During this waiting time, the wound status can change. However, our in situ biosensor can instantly, in real-time, determine the presence of bacteria from a low concentration (3.0E+04 CFU/cm$^2$) to a higher concentration to prevent any tissue damage and infection from spreading. The biosensor can roughly determine the severity of infection by monitoring the relative darkness of the green color.

Early detection of bacteria present in wounds can prevent infection by detecting the presence of bacteria in a concentration lower than critical colonization concentration. Controlling bacteria growth before reaching the infection stage can prevent the spread of infection as well as tissue damage. Moreover, it reduces the misusage of antibiotics and the chance of bacteria resistance. Therefore, in this study, the aim was to enhance the sensitivity of the biosensors for bacteria detection. The fabricated biosensors are nanofibrous membranes based on polyurethane, polyvinylpyrrolidone and hemicyanine dye. The hemicyanine dye has an ester bond in its structure that can be cleaved by secreted lipase from bacteria. Therefore, the yellow dye will be cleaved in the presence of bacteria, facilitating more efficient intramolecular charge transfer and leading to a green color change. In order to increase the sensitivity of the nanofibrous biosensors with a core-shell structure, we incorporated a surfactant e.g. Tween 80 in the shell composition. Tween 80 with an optimum concentration can increase the lipase activity of bacteria and facilitates color-changing in a lower concentration. Tween 80 plays two roles in increasing the sensitivity of biosensors. Firstly, it provides an interfacial surface area between the lipase and substrate (HCy), which facilities a higher rate of cleavage, and secondly, it increases lipase activity by unmasking the activation site of the lipase. However, the high concentration of Tween 80 can have adverse effects and inhibit the lipase activity due to strong interaction with lipase that can denature it. Therefore, different concentrations of Tween 80 from 0 to 4% were examined in the presence of three different bacteria, namely *E. coli, P. aeruginosa* and MRSA. The results showed that the optimum concentration of Tween 80, which leads to a high lipase activity in a lower concentration of bacteria and works well for all types of tested bacteria, is 0.5%. In addition to incorporating Tween 80, we evaluated the role of fiber alignment on the sensitivity of the biosensors. The effect of alignments on the fate of stem cells or the behavior of human cells have been explored vastly, but in this study, we demonstrate that it also can affect bacterial cell. The cross-aligned fibers are more favorable for bacteria interaction, and the alignment helps to change the configuration of lipase domains and unmask the activation site. Overall, the fabricated cross-aligned biosensors incorporated with 0.5% Tween 80 can help early detection of infection in real-time and in situ ($\sim$3.0E+04 CFU/cm$^2$) without requiring highly advanced technology or trained personnel.

Additional testing has been conducted to determine the chromogenic fiber response of the biosensor of the present invention to various concentrations of ESKAPEE bacteria (*Enterococcus faecium, Staphylococcus aureus, Klebsiella pneumoniae, Acinetobacter baumannii, Pseudomonas aeruginosa, Enterobacter* species, and *Escherichia coli*). Biosensor samples were tested against five strains of each ESKAPEE bacteria. The fabricated samples of cross-aligned biosensors incorporated 0.5% Tween 80. The results of these tests are presented in the following table, indicating the detection threshold of presence and the time to reach color change after exposure of a biosensor sample to each bacteria strain.

| Test Results: ESKAPEE Bacteria Strains (5 strains per bacteria) |
| --- |
| *E. Faecium*- All 5 strains detected at 10^5 threshold under 2 hours |
| *S. Aureus*- 4 of the 5 strains detected at 10^4-10^6 threshold under 2 hour |
| *K. Pneumoniae*- All 5 strains detected at 10^5-10^6 threshold in under 1 hour |
| *A. Baumannii*- All 5 strains detected at 10^6 threshold in under 1 hour |
| *P. aeruginosa*- All 5 strains detected at 10^4-10^5 threshold in under 1 hour |
| *E. Cloacae*- 4 of the 5 strains detected at 10^4-10^6 threshold under 2 hours |
| *E. Coli*- All 5 strains detected at 10^5-10^6 threshold in under 1 hour |

Completed testing showed that the biosensors of the present invention can detect ESKAPEE pathogens and provide a visible alert via color change of the biosensor. Further, the biosensor samples detected 33 of the 35 ESKAPEE strains tested at or below 106 CFU/cm$^2$. The other two ESKAPEE strains were detected at a higher concentration than 106 CFU/cm$^2$. The color change detection of the biosensors varied across different strains and replicates.

Referring to FIG. 12, it is important to recognize that some strains of fungi produce lipase and can be detected by the biosensor of the present invention. As shown in FIG. 12, testing of various samples of the biosensor demonstrated a clear and rapid color-changing response in the presence of two different fungi: *Candida albicans* and *Candida aruis*. Two other fungi, *M. circinelloides*, and *F. oxysporum* were detected albeit after several days of incubation. The shell of the core-shell nanofiber comprising the samples included the HCy dye and Tween 80.

Three of four biosensor samples had color change compared to a negative control at Time 0 for both *Candida albicans* and *Candida auris*. *Candida albicans* reached a concentration of $1.55\times10^5$ CFU/cm$^2$ at color change, while *Candida auris* reached a concentration of $4.18\times10^3$ CFU/cm$^2$ at color change. After overnight incubation, the color change of the three sensors on each fungal pathogen persisted.

While the preferred embodiments of the invention have been described above, it will be recognized and understood that various modifications may be made therein, and the appended claims are intended to cover all such modifications which may fall within the spirit and scope of the invention.

In the preceding description, for purposes of explanation, numerous details are set forth in order to provide a thorough understanding of the embodiments. However, it will be apparent to one skilled in the art that these specific details are not required. For example, specific details are not provided as to whether the embodiments described herein are implemented using computer hardware or software, or a combination thereof.

The above-described embodiments are intended to be examples only. Alterations, modifications and variations can be affected to the particular embodiments by those of skill in the art. The scope of the claims should not be limited by the particular embodiments set forth herein, but should be construed in a manner consistent with the specification as a whole.

The invention claimed is:

1. A biosensor comprising:
   a core-shell nanofiber having a colorimetric probe incorporated in the shell,
   wherein the colorimetric probe changes color in the presence of pathogens at a tunable specific threshold,
   wherein said colorimetric probe comprises a hemicyanine dye and a non-ionic surfactant incorporated into a shell composition of core-shell nanofibers, and
   wherein said non-ionic surfactant is polysorbate 80.

2. The biosensor of claim 1, wherein a concentration of said non-ionic surfactant is in the range of 0.1% to 4%.

3. The biosensor of claim 1, wherein a concentration of said non-ionic surfactant is in the range of 0.5% to 2%.

4. A process for fabricating a chromatic biosensor comprising: coaxially electrospinning a core material within a shell material to thereby form a plurality of chromatic core-shell nanofibers; controlling alignment of said core-shell nanofibers produced to enhance sensitivity to bacterial lipase,
   wherein, the core material comprises a biocompatible polymer and the shell material comprises a biocompatible polymer, a hemicyanine dye, and a non-ionic surfactant,
   wherein said surfactant is selected from any of polysorbate 10, polysorbate 40, polysorbate 60, polysorbate 80, octoxynol-9, and sodium dodecyl sulfate.

5. The process of claim 4, wherein said chromatic core-shell nanofiber further comprises polyurethane and polyvinylpyrrolidone.

6. The biosensor of claim 5, wherein said colorimetric probe is configured to change color when exposed to any of *Enterococcus faecium, Staphylococcus aureus, Klebsiella pneumoniae, Acinetobacter baumannii, Pseudomonas aeruginosa, Enterobacter* species, *Escherichia coli, Candida albicans*, and *Candida auris*.

\*  \*  \*  \*  \*